(12) United States Patent
Merla et al.

(10) Patent No.: US 7,229,991 B2
(45) Date of Patent: Jun. 12, 2007

(54) SUBSTITUTED 5-AMINOMETHYL-1H-PYRROLE-2-CARBOXAMIDES

(75) Inventors: Beatrix Merla, Aachen (DE); Corinna Sundermann, Aachen (DE); Utz-Peter Jagusch, Aachen (DE); Werner Englberger, Stolberg (DE); Hagen-Heinrich Hennies, Simmerath (DE); Babette-Yvonne Kögel, Langerwehe-Hamich (DE)

(73) Assignee: Gruenenthal GmbH, Aachen (DE)

( * ) Notice: Subject to any disclaimer, the term of this patent is extended or adjusted under 35 U.S.C. 154(b) by 96 days.

(21) Appl. No.: 11/155,764

(22) Filed: Jun. 20, 2005

(65) Prior Publication Data

US 2005/0288342 A1 Dec. 29, 2005

Related U.S. Application Data

(63) Continuation of application No. PCT/EP03/14496, filed on Dec. 18, 2003.

(30) Foreign Application Priority Data

Dec. 20, 2002 (DE) ................ 102 61 131

(51) Int. Cl.
*A61K 31/5377* (2006.01)
*A61K 31/40* (2006.01)
*C07D 413/06* (2006.01)
*C07D 401/06* (2006.01)
*C07D 207/335* (2006.01)

(52) U.S. Cl. ............. 514/235.5; 514/326; 514/422; 514/423; 544/141; 546/208; 548/518; 548/561

(58) Field of Classification Search ........... None
See application file for complete search history.

(56) References Cited

U.S. PATENT DOCUMENTS 3,551,571 A 12/1970 Pachter et al.
6,849,730 B2 * 2/2005 Lindsey et al. ............. 540/145

FOREIGN PATENT DOCUMENTS

WO WO 02/02521 A2 1/2002
WO WO 02/057253 A2 7/2002

OTHER PUBLICATIONS

Chakraborty, et al., Development of 5-(aminomethyl)pyrrole-2-carboxylic acid as a constrained surrogate of Gly-ΔAla and its appplication in peptidomimetic studies. Tetrahedron Letters 43 (2002) 2589-2592.
Scott, et al., Piperazinylalkyl Heterocycles as Potential Antipsychotic Agents. J. Med. Chem. 38 (1995) 4198-4210.
Oliver H. Lowry et al., "Protein Measurement with the Folin Phenol Reagent", May 28, 1951, pp. 265-275, Washington University School of Medicine, Department of Pharmacology, St. Louis, Missouri, USA.

Martin Ch. Frink et al., "Influence of Tramadol on Neurotransmitter Systems of the Rat Brain", Arzneim-Forsch./ Drug Res., 1996, pp. 1029-1036, vol. 46 (III), Nr. 11.
L.C. Hendershot et al., "Antagonism of the Frequency of Phenylquinone-Induced Writing in the Mouse by Weak Analgesics and Nonanalgesics", Sep. 19, 1958, pp. 237-240, vol. 125, The Biomedical Research Laboratory, The Dow Chemical Company, Midland, Michigan, USA.
E.G. Gray et al., "The Isolation of Nerve Endings from Brain: An Electron-Microscopic Study of Cell Fragments Derived by Homogenization and Centrifugation", Journal of Anatomy, pp. 79-88, vol. 96, Part 1 (1962).
Andrew J. Carpenter et al., The Scope and Limitations of Carboxamide-Induced β- Directed Metalation of 2-Substituted Furan, Thiophene, and 1-Methylpyrrole Derivatives. Application of Method to Syntheses of 2,3-Disubstituted Thiophenes and Furans, J. Org. Chem., 1985, pp. 4362-4368, vol. 50, No. 22, American Chemical Society.
Beatrix Merla et al., "Efficient Synthesis of γ-Oxo- and γ-Hydroxy-α-amino Acids", Synthesis, Nov. 1998, pp. 1609-1614.
von Claudia Betschart et al., "Scope and Limitations of the Reductive Coupling of Aromatic Aldimine Derivatives with Formation of 1,2-Diarylethylenediame Units, Using Low-Valent Titanium Regeants", Helvetica Chimica Acta, 1988, pp. 1999-2023, vol. 71.
Mark A. Longer et al., "Sustained-Release Drug Delivery Systems", pp. 1644-1661, Chapter 92, (1985).
Stuart C. Porter, PH.D, "Coating of Pharmaceutical Dosage Forms", pp. 1633-1643, Chapter 91 (1985).
Robert E. King, PH.D et al., "Oral Solid Dosage Forms", pp. 1603-1632, Chapter 90 (1985).
Edward G. Ripple, Ph.D., "Powders", pp. 1585-1602, Chapter 89 (1985).
Lawrence H. Block, PH.D., Medicated Applications, pp. 1567-1584, Chapter 88 (1985).
John D. Mullins, PH.D., "Ophthalmic Preparations", pp. 1553-1566, Chapter 87 (1985).
Salvatore J. Turco, Pharm.D et al., "Intravenous Admixtures", pp. 1542-1552, Chapter 86 (1985).
Kenneth E. Avis, DSC, "Parenteral Preparations", pp. 1518-1541, Chapter 85 (1985).

(Continued)

Primary Examiner—Kamal A. Saeed
Assistant Examiner—Andrew B. Freistein
(74) Attorney, Agent, or Firm—Crowell & Moring LLP

(57) ABSTRACT

5-aminomethyl-1H-pyrrole-2-carboxylic acid amide compounds corresponding to formula I

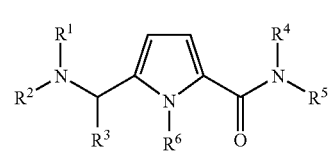

and processes for the production thereof. Pharmaceutical preparations containing these compounds and the use of these compounds for the production of pharmaceutical preparations and in related treatment methods.

33 Claims, No Drawings

OTHER PUBLICATIONS

J. G. Narin, PH.D., "Solutions, Emulsions, Suspensions and Extractives", pp. 1492-1517, Chapter 84 (1985).

Clyde R. Erskine, Jr, "Quality Assurance and Control", pp. 1487-1491, Chapter 83 (1985).

Carl J. Lintner, PH.D., "Stability of Pharmaceutical Products", pp. 1478-1486, Chapter 82 (1985).

Robert L. Giles, B.A. et al., "Plastic Packaging Materials", pp. 1473-1477, Chapter 81 (1985).

Frederick P. Siegel, PH.D., "Tonicity, Osmoticity, Osmolality, and Osmolarity", pp. 1455-1472, Chapter 80 (1985).

G. Briggs Phillips, PH.D., "Sterilization", pp. 1443-1454, Chapter 79 (1985).

Adelbert M. Knevel, PH.D., "Separation", pp. 1432-1442, Chapter 79 (1985).

Anthony R. Disanto, PH.D., "Bioavailability and Bioequivalency Testing", pp. 1424-1431, Chapter 77 (1985).

* cited by examiner

SUBSTITUTED 5-AMINOMETHYL-1H-PYRROLE-2-CARBOXAMIDES

CROSS REFERENCE TO RELATED APPLICATIONS

This application is a continuation of International Patent Application No. PCT/EP2003/014496, filed Dec. 18, 2003, designating the United States of America, and published in German as WO 2004/058707 A1, the entire disclosure of which is incorporated herein by reference. Priority is claimed based on German Patent Application No. 102 61 131.9, filed Dec. 20, 2002.

FIELD OF THE INVENTION

The present invention relates to substituted 5-aminomethyl-1H-pyrrole-2-carboxylic acid amides, to a process for the production thereof, to pharmaceutical preparations containing these compounds and to the use of these compounds for the production of pharmaceutical preparations and in related treatment methods.

BACKGROUND OF THE INVENTION

Pain is one of the basic clinical symptoms. There is a worldwide need for effective pain treatments. The urgency of the requirement for therapeutic methods for providing tailored and targeted treatment of chronic and non-chronic pain, this being taken to mean pain treatment which is effective and satisfactory from the patient's standpoint, is evident from the large number of scientific papers relating to applied analgesia and to basic nociception research which have appeared in recent times.

Conventional opioids, such as for example morphine, are effective in the treatment of severe to very severe pain, but they exhibit unwanted accompanying symptoms, such as for example respiratory depression, vomiting, sedation or constipation. Research is being carried out worldwide into other pain-relieving agents.

SUMMARY OF THE INVENTION

One object of certain embodiments of the present invention is to provide novel active ingredients which are in particular suitable for use in pharmaceutical preparations, preferably in pharmaceutical preparations for combating, inhibiting and alleviating pain.

This object is achieved by the substituted 5-aminomethyl-1H-pyrrole-2-carboxylic acid amides, according to the invention, of the general formula I below.

It has surprisingly been found that the substituted 5-aminomethyl-1H-pyrrole-2-carboxylic acid amides according to the invention of the general formula I below exhibit elevated affinity for the ORL ("opioid receptor like")-1 receptor as well as for the μ opioid receptor and are accordingly suitable for regulating these receptors. The substituted 5-aminomethyl-1H-pyrrole-2-carboxylic acid amides according to the invention of the general formula I below furthermore bring about inhibition of noradrenalin uptake and inhibition of 5-hydroxytryptamine (5-HT) uptake.

The substituted 5-aminomethyl-1H-pyrrole-2-carboxylic acid amides according to the invention of the general formula I below in particular exhibit a marked activity in combatting pain, preferably chronic pain and/or acute pain and/or neuropathic pain. The substituted 5-aminomethyl-1H-pyrrole-2-carboxamides according to the invention are furthermore also suitable for the treatment of withdrawal symptoms, memory disorders, neurodegenerative diseases, preferably Parkinson's disease, Huntington's chorea or Alzheimer's disease, epilepsy, disorders of the cardiovascular system, water retention conditions, intestinal motility (diarrhoea), urinary incontinence, anorexia, pruritus, depression, tinnitus, sexual dysfunction, preferably erectile dysfunction, respiratory diseases, or for diuresis, for influencing the cardiovascular system, preferably for vasodilating the arteries, for suppression of the urinary reflex, for anxiolysis, for regulating the electrolyte balance, for regulating, preferably stimulating, food intake, for reducing the addictive potential of opioids, in particular of morphine, for modulating locomotor activity, for influencing the action of μ agonists, in particular morphine.

The present invention accordingly provides substituted 5-aminomethyl-1H-pyrrole-2-carboxylic acid amides of the following general formula I,

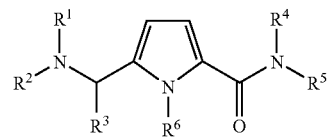

in which

R$^1$ denotes hydrogen, a linear or branched, saturated or unsaturated, optionally at least mono-substituted aliphatic residue, a saturated or unsaturated, optionally at least mono-substituted, cycloaliphatic residue optionally comprising at least one heteroatom as a ring member and optionally attached via an optionally at least mono-substituted alkylene group, an optionally at least mono-substituted aryl or heteroaryl residue or an optionally at least mono-substituted aryl or heteroaryl residue attached via an optionally substituted alkylene group, R$^2$ denotes a linear or branched, saturated or unsaturated, optionally at least mono-substituted aliphatic residue, a saturated or unsaturated, optionally at least mono-substituted, cycloaliphatic residue optionally comprising at least one heteroatom as a ring member and optionally attached via an optionally at least mono-substituted alkylene group, an optionally at least mono-substituted aryl or heteroaryl residue or an optionally at least mono-substituted aryl or heteroaryl residue attached via an optionally substituted alkylene group, or R$^1$ and R$^2$, together with the nitrogen atom joining them as a ring member, form a saturated or unsaturated, optionally at least mono-substituted cycloaliphatic residue optionally comprising at least one further heteroatom as a ring member, R$^3$ denotes an optionally at least mono-substituted aryl or heteroaryl residue, an ester group or a carboxy group, R$^4$ and R$^5$, identical or different, denote hydrogen, a linear or branched, saturated or unsaturated, optionally at least mono-substituted aliphatic residue, a saturated or unsaturated, optionally at least mono-substituted, cycloaliphatic residue optionally comprising at least one heteroatom as a ring member and optionally attached via an optionally at least mono-substituted alkylene group, an optionally at least mono-substituted aryl or heteroaryl residue or an optionally at least mono-substituted aryl or heteroaryl residue attached via an optionally substituted alkylene group, or $R^4$ and $R^5$, together with the nitrogen atom joining them as a ring member, form a saturated or unsaturated, optionally at least mono-substituted cycloaliphatic residue optionally comprising at least one further heteroatom as a ring member, and $R^6$ denotes a linear or branched, saturated or unsaturated, optionally at least mono-substituted aliphatic residue, a saturated or unsaturated, optionally at least mono-substituted, cycloaliphatic residue optionally comprising at least one heteroatom as a ring member and optionally attached via an optionally at least mono-substituted alkylene group, an optionally at least mono-substituted aryl or heteroaryl residue or an optionally at least mono-substituted aryl or heteroaryl residue attached via an optionally at least mono-substituted alkylene group, optionally in the form of the pure stereoisomers thereof, in particular enantiomers or diastereomers, the racemates thereof or in the form of mixtures of the stereoisomers, in particular the enantiomers, diastereomers or rotamers, in any desired mixing ratio, or in each case in the form of the acids or bases thereof or in the form of the salts thereof, in particular the physiologically acceptable salts, or in each case in the form of the solvates thereof, in particular the hydrates.

Preferred substituted 5-aminomethyl-1H-pyrrole-2-carboxylic acid amides according to the invention of the general formula I are those in which $R^1$ denotes hydrogen, a linear or branched, saturated or unsaturated, optionally at least mono-substituted aliphatic $C_{1-6}$ residue, a saturated or unsaturated, optionally at least monosubstituted cycloaliphatic $C_{3-8}$ residue optionally comprising at least one heteroatom as a ring member and optionally attached via an optionally at least mono-substituted $C_{1-3}$ alkylene group, an optionally at least mono-substituted five- or six-membered aryl or heteroaryl residue or an optionally at least mono-substituted, five- or six-membered aryl or heteroaryl residue attached via an optionally substituted $C_{1-3}$ alkylene group, preferably a linear or branched, saturated aliphatic $C_{1-3}$ residue, particularly preferably a methyl residue and the remaining residues $R^2$-$R^6$ have the above-stated meaning, optionally in the form of the pure stereoisomers thereof, in particular enantiomers or diastereomers, the racemates thereof or in the form of mixtures of the stereoisomers, in particular the enantiomers, diastereomers or rotamers, in any desired mixing ratio, or in each case in the form of the acids or bases thereof or in the form of the salts thereof, in particular the physiologically acceptable salts, or in each case in the form of the solvates thereof, in particular the hydrates.

Likewise preferred substituted 5-aminomethyl-1H-pyrrole-2-carboxylic acid amides according to the invention of the general formula I are those in which $R^2$ denotes a linear or branched, saturated or unsaturated, optionally at least mono-substituted aliphatic $C_{1-6}$ residue, a saturated or unsaturated, optionally at least monosubstituted cycloaliphatic $C_{3-8}$ residue optionally comprising at least one heteroatom as a ring member and optionally attached via an optionally at least mono-substituted $C_{1-3}$ alkylene group, an optionally at least mono-substituted, five- or six-membered aryl or heteroaryl residue or an optionally at least mono-substituted, five- or six-membered aryl or heteroaryl residue attached via an optionally substituted $C_{1-3}$ alkylene group, preferably a linear or branched, saturated aliphatic $C_{1-3}$ residue, particularly preferably a methyl residue and the remaining residues $R^1$ and $R^3$ to $R^6$ have the above-stated meaning, optionally in the form of the pure stereoisomers thereof, in particular enantiomers or diastereomers, the racemates thereof or in the form of mixtures of the stereoisomers, in particular the enantiomers, diastereomers or rotamers, in any desired mixing ratio, or in each case in the form of the acids or bases thereof or in the form of the salts thereof, in particular the physiologically acceptable salts, or in each case in the form of the solvates thereof, in particular the hydrates.

Further preferred substituted 5-aminomethyl-1H-pyrrole-2-carboxylic acid amides according to the invention of the general formula I are those, in which the residues $R^1$ and $R^2$, together with the nitrogen atom joining them as a ring member, form a saturated or unsaturated, optionally at least mono-substituted, five- or six-membered cycloaliphatic residue, which optionally comprises at least one further heteroatom selected from the group consisting of N, O and S as a ring member, preferably, together with the nitrogen atom joining them as a ring member, form a saturated, five- or six-membered cycloaliphatic residue optionally comprising oxygen as a further ring member, particularly preferably together denote a $(CH_2)_4$, $(CH_2)_5$ or $(CH_2)_2$—O—$(CH_2)_2$ residue which, with the nitrogen atom joining them as a ring member, forms a heterocycle, and in each case the remaining residues $R^3$ to $R^6$ have the above-stated meaning, optionally in the form of the pure stereoisomers thereof, in particular enantiomers or diastereomers, the racemates thereof or in the form of mixtures of the stereoisomers, in particular the enantiomers, diastereomers or rotamers, in any desired mixing ratio, or in each case in the form of the acids or bases thereof or in the form of the salts thereof, in particular the physiologically acceptable salts, or in each case in the form of the solvates thereof, in particular the hydrates.

Further preferred substituted 5-aminomethyl-1H-pyrrole-2-carboxylic acid amides according to the invention of the general formula I are those, in which $R^3$ denotes an unsubstituted or at least mono-substituted, five- or six-membered aryl or heteroaryl residue or an aryl ester, heteroaryl ester or alkyl ester group, preferably an optionally at least mono-substituted phenyl residue or an alkyl ester group with $C_{1-3}$, preferably $C_{1-2}$, in the alkyl moiety, and in each case the residues $R^1$, $R^2$ and $R^4$ to $R^6$ have the above-stated meaning, optionally in the form of the pure stereoisomers thereof, in particular enantiomers or diastereomers, the racemates thereof or in the form of mixtures of the stereoisomers, in particular the enantiomers, diastereomers or rotamers, in any desired mixing ratio, or in each case in the form of the acids or bases thereof or in the form of the salts thereof, in particular the physiologically acceptable salts, or in each case in the form of the solvates thereof, in particular the hydrates.

Further preferred substituted 5-aminomethyl-1H-pyrrole-2-carboxylic acid amides according to the invention of the general formula I are those in which the residues $R^4$ and $R^5$, identical or different, denote hydrogen, a linear or branched, saturated or unsaturated, optionally at least mono-substituted aliphatic $C_{1-6}$ residue, a saturated or unsaturated, optionally at least monosubstituted cycloaliphatic $C_{3-8}$ residue optionally comprising at least one heteroatom as a ring member and optionally attached via an optionally at least mono-substituted $C_{1-3}$ alkylene group, an optionally at least mono-substituted, five- or six-membered aryl or heteroaryl residue or an optionally at least mono-substituted, five- or six-membered aryl or heteroaryl residue attached via an optionally substituted $C_{1-3}$ alkylene group, preferably hydrogen, methyl, ethyl, n-propyl, iso-propyl, n-butyl, cyclopentyl, cyclohexyl, benzyl or phenethyl, and in each case the residues $R^1$ to $R^3$ and $R^6$ have the above-stated meaning, optionally in the form of the pure stereoisomers thereof, in particular enantiomers or diastereomers, the racemates thereof or in the form of mixtures of the stereoisomers, in particular the enantiomers, diastereomers or rotamers, in any desired mixing ratio, or in each case in the form of the acids or bases thereof or in the form of the salts thereof, in particular the physiologically acceptable salts, or in each case in the form of the solvates thereof, in particular the hydrates.

Likewise preferred substituted 5-aminomethyl-1H-pyrrole-2-carboxylic acid amides according to the invention of the general formula I are those, in which the residues $R^4$ and $R^5$, together with the nitrogen atom joining them as a ring member, form a saturated or unsaturated, optionally at least mono-substituted, five-, six- or seven-membered cycloaliphatic residue, which optionally comprises at least one further heteroatom selected from the group consisting of N, O and S as a ring member, preferably, together with the nitrogen atom joining them as a ring member, form a saturated, five- or six-membered cycloaliphatic residue optionally comprising oxygen as a further ring member, particularly preferably together denote a $(CH_2)_4$, $(CH_2)_5$ or $(CH_2)_2$—O—$(CH_2)_2$ residue which, with the nitrogen atom joining them as a ring member, forms a heterocycle, and in each case the remaining residues $R^1$ to $R^3$ and $R^6$ have the above-stated meaning, optionally in the form of the pure stereoisomers thereof, in particular enantiomers or diastereomers, the racemates thereof or in the form of mixtures of the stereoisomers, in particular the enantiomers, diastereomers or rotamers, in any desired mixing ratio, or in each case in the form of the acids or bases thereof or in the form of the salts thereof, in particular the physiologically acceptable salts, or in each case in the form of the solvates thereof, in particular the hydrates.

Further preferred substituted 5-aminomethyl-1H-pyrrole-2-carboxylic acid amides according to the invention of the general formula I are those, in which $R^6$ denotes a linear or branched, saturated or unsaturated, optionally at least mono-substituted aliphatic $C_{1-6}$ residue, a saturated or unsaturated, optionally at least monosubstituted cycloaliphatic $C_{3-8}$ residue optionally comprising at least one heteroatom as a ring member and optionally attached via an optionally at least mono-substituted $C_{1-3}$ alkylene group, an optionally at least mono-substituted, five- or six-membered aryl or heteroaryl residue or an optionally at least mono-substituted, five- or six-membered aryl or heteroaryl residue attached via an optionally at least mono-substituted $C_{1-3}$ alkylene group, preferably a linear or branched, saturated aliphatic $C_{1-3}$ residue, particularly preferably a methyl residue and the residues $R^1$ to $R^5$ in each case have the above-stated meaning, optionally in the form of the pure stereoisomers thereof, in particular enantiomers or diastereomers, the racemates thereof or in the form of mixtures of the stereoisomers, in particular the enantiomers, diastereomers or rotamers, in any desired mixing ratio, or in each case in the form of the acids or bases thereof or in the form of the salts thereof, in particular the physiologically acceptable salts, or in each case in the form of the solvates thereof, in particular the hydrates.

If one of the above-stated residues $R^1$ to $R^6$ denotes an aliphatic or cycloaliphatic residue which is mono- or polysubstituted, the substituents may preferably be selected from the group consisting of halogen, hydroxy, CN, $CF_3$, $CHF_2$, $CH_2F$, $C_{1-6}$ alkyl, $C_{1-6}$ alkoxy and optionally at least mono-substituted phenyl, particularly preferably from the group consisting of F, Cl, Br and hydroxy. If the phenyl substituent is itself mono- or polysubstituted, the substituents thereof may preferably be selected from the group consisting of hydroxy, CN, $CF_3$, $CHF_2$, $CH_2F$, $C_{1-6}$ alkyl and $C_{1-6}$ alkoxy.

If the above-stated residues $R^1$ to $R^6$ comprise a mono- or polysubstituted alkylene group, the substituents thereof may preferably be selected from the group consisting of halogen, hydroxy, CN, $CF_3$, $CHF_2$, $CH_2F$, $C_{1-6}$ alkoxy and optionally at least mono-substituted phenyl, particularly preferably from the group consisting of F, Cl, Br and hydroxy. If the phenyl substituent is itself mono- or polysubstituted, the substituents thereof may preferably be selected from the group consisting of hydroxy, CN, $CF_3$, $CHF_2$, $CH_2F$, $C_{1-6}$ alkyl and $C_{1-6}$ alkoxy.

If one of the above-stated residues $R^1$ to $R^6$ comprises a mono- or polysubstituted aryl or heteroaryl residue, the corresponding substituents may preferably be selected from the group consisting of halogen, hydroxy, CN, $CF_3$, $CHF_2$, $CH_2F$, $NO_2$, $NH_2$, $C_{1-6}$ alkyl, $C_{1-6}$ alkoxy and optionally at least mono-substituted phenyl, particularly preferably from the group consisting of F, Cl, Br, hydroxy, $OCH_3$ and $CH_3$. If the phenyl substituent is itself mono- or polysubstituted, the substituents thereof may preferably be selected from the group consisting of hydroxy, CN, $CF_3$, $CHF_2$, $CH_2F$, $C_{1-6}$ alkyl and $C_{1-6}$ alkoxy.

If one of the above-stated residues $R^1$ to $R^6$ denotes a cycloaliphatic residue with at least one heteroatom or a heteroaryl residue, the heteroatoms, unless stated otherwise, may preferably be selected from the group consisting of oxygen, nitrogen and sulfur.

Suitable aliphatic residues, which are optionally mono- or polysubstituted, may for example be selected from the group consisting of methyl, ethyl, n-propyl, iso-propyl, n-butyl, sec-butyl, tert.-butyl, n-pentyl, iso-pentyl, neopentyl, n-hexyl, 2-hexyl, n-heptyl, n-octyl, vinyl, ethynyl, propenyl, propynyl, butenyl, butynyl, pentenyl, pentynyl, hexenyl, hexynyl, heptyl, heptynyl, octenyl and octyl.

Suitable cycloaliphatic residues, which are optionally mono- or polysubstituted and/or optionally comprise at least one heteroatom, may for example be selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, pyrrolidinyl, piperidinyl, piperazinyl and morpholinyl.

Suitable alkylene groups, which are optionally mono- or polysubstituted, may for example be selected from the group consisting of methylene —$(CH_2)$—, ethylene —$(CH_2)_2$—, propylene —$(CH_2)_3$—, butylene —$(CH_2)_4$—, pentylene —$(CH_2)_5$— and hexylene —$(CH_2)_6$—, in each case optionally also branched.

Suitable aryl residues, which are optionally mono- or polysubstituted, are for example phenyl or naphthyl, preferably phenyl.

Suitable heteroaryl residues, which are optionally mono- or polysubstituted, may for example be selected from the group consisting of pyrrolyl, furyl, thienyl, pyrazolyl, imidazolyl, pyridinyl, pyridazinyl and pyrimidinyl.

Very particularly preferred substituted 5-aminomethyl-1H-pyrrole-2-carboxylic acid amides according to the invention are those selected from the group consisting of 5-[dimethylamino-(4-fluoro-phenyl)-methyl]-1H-methyl-1H-pyrrole-2-carboxylic acid cyclohexylamide, 5-[dimethylamino-(4-fluoro-phenyl)-methyl]-1-methyl-1H-pyrrole-2-carboxylic acid butylamide, {5-[dimethylamino-(4-fluoro-phenyl)-methyl]-1-methyl-1H-pyrrol-2-yl}-pyrrolidin-1-yl-methanone, 5-[dimethylamino-(4-bromo-phenyl)-methyl]-1-methyl-1H-pyrrole-2-carboxylic acid cyclohexylamide, 5-[dimethylamino-(4-bromo-phenyl)-methyl]-1-methyl-1H-pyrrole-2-carboxylic acid butylamide,
{5-[(4-bromo-phenyl)-dimethylamino-methyl]-1-methyl-1H-pyrrol-2-yl}-pyrrolidin-1-yl-methanone,
5-[(4-bromo-phenyl)-dimethylamino-methyl]-1-methyl-1H-pyrrole-2-carboxylic acid phenethyl-amide,
{5-[(4-bromo-phenyl)-dimethylamino-methyl]-1-methyl-1H-pyrrol-2-yl}-morpholin-4-yl-methanone,
5-(dimethylamino-phenyl-methyl)-1-methyl-1H-pyrrole-2-carboxylic acid cyclohexylamide,
5-(dimethylamino-phenyl-methyl)-1-methyl-1H-pyrrole-2-carboxylic acid butylamide,
[5-(dimethylamino-phenyl-methyl)-1-methyl-1H-pyrrol-2-yl]-pyrrolidin-1-yl-methanone,
(5-butylcarbamoyl-1-methyl-1H-pyrrol-2-yl)-dimethylamino-acetic acid ethyl ester,
(5-cyclohexylcarbamoyl-1-methyl-1H-pyrrol-2-yl)-dimethylamino-acetic acid ethyl ester,
(5-butylcarbamoyl-1-methyl-1H-pyrrol-2-yl)-piperidin-1-yl-acetic acid ethyl ester and
(5-cyclohexylcarbamoyl-1-methyl-1H-pyrrol-2-yl)-piperidin-1-yl-acetic acid ethyl ester,
optionally in the form of the pure stereoisomers thereof, in particular enantiomers or diastereomers, the racemates thereof or in the form of mixtures of the stereoisomers, in particular the enantiomers, diastereomers or rotamers, in any desired mixing ratio, or in each case in the form of the acids or bases thereof or in the form of the salts thereof, in particular the physiologically acceptable salts, particularly preferably the hydrochlorides, or in each case in the form of the solvates thereof, in particular the hydrates.

The present invention also provides a process for the production of substituted 5-aminomethyl-1H-pyrrole-2-carboxylic acid amides according to the invention of the general formula I, in accordance with which a substituted 1H-pyrrole-2-carboxylic acid amide of the general formula II

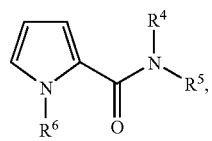

in which the residues $R^4$, $R^5$ and $R^6$ have the above-stated meaning, are reacted using conventional methods known to the person skilled in the art, preferably in a suitable solvent, such as for example $CH_2Cl_2$, $CH_3CN$, dimethylformamide (DMF) or mixtures of at least two of these solvents, at room temperature (approx. 20-25° C.) with an iminium salt of the general formula III,

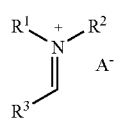

in which $R^1$ to $R^3$ have the above-stated meaning and $A^-$ denotes a suitable anion, preferably $Cl^-$, $AlCl_4^-$, $Br^-$, $I^-$ or $CF_3$—$SO_3^-$ (triflate anion), to yield a substituted 5-aminomethyl-1H-pyrrole-2-carboxylic acid amide according to the invention of the general formula I and this latter compound is optionally purified using conventional methods known to the person skilled in the art, preferably by extraction, and optionally isolated.

The compounds of the general formula II may be produced using conventional methods known to the person skilled in the art, for example from the commercially obtainable reagents of the general formula IV

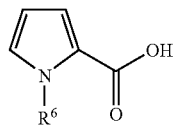

in which $R^6$ has the above-stated meaning, such as for example described in A. J. Carpenter, D. J. Chadwick, Journal of Organic Chemistry, 1985, 50, pages 4362-4368. The corresponding literature description is hereby introduced as a reference and is deemed to be part of the disclosure.

The iminium salts of the general formula III may likewise be obtained using conventional methods known to the person skilled in the art, for example from the corresponding aminals of the general formula V below

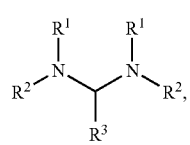

in which the residues $R^1$, $R^2$ and $R^3$ have the above-stated meaning, as for example described in D. Seebach et al., Helv. Chim. Acta 1988, 71, pages 1999-2001 and N. Risch et al., Synthesis 1998, 11, pages 1609-1614. The corresponding literature descriptions are hereby introduced as a reference and are deemed to be part of the disclosure.

The aminals of the general formula V may also be produced in accordance with methods known from the literature, as for example described in D. Seebach et al., Helv. Chim. Acta 1988, 71, pages 1999-2001 and N. Risch et al., Synthesis 1998, 11, pages 1609-1614. The corresponding literature descriptions are hereby introduced as a reference and are deemed to be part of the disclosure.

The substituted 5-aminomethyl-1H-pyrrole-2-carboxylic acid amides according to the invention of the general formula I and corresponding stereoisomers may be isolated not only in the form of the free bases or free acids thereof, but also in the form of corresponding salts.

The free bases of the respective 5-aminomethyl-1H-pyrrole-2-carboxylic acid amides according to the invention of the general formula I and corresponding stereoisomers may, for example, be converted into the corresponding physiologically acceptable salts by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid.

The free bases of the respective 5-aminomethyl-1H-pyrrole-2-carboxylic acid amides according to the invention of the general formula I and corresponding stereoisomers may preferably be converted into the corresponding hydrochlorides by combining the compounds of the general formula I or corresponding stereoisomers as free bases dissolved in a suitable organic solvent, such as for example butan-2-one (methyl ethyl ketone), with trimethylsilyl chloride (TMSCI).

The free bases of the respective 5-aminomethyl-1H-pyrrole-2-carboxylic acid amides of the general formula I and corresponding stereoisomers may likewise be converted into the corresponding physiologically acceptable salts with the free acid or a salt of a sugar substitute, such as for example saccharin, cyclamate or acesulfame.

The free acids of the respective 5-aminomethyl-1H-pyrrole-2-carboxylic acid amides of the general formula I and corresponding stereoisomers may accordingly be converted into the corresponding physiologically acceptable salts by reaction with a suitable base.

The 5-aminomethyl-1H-pyrrole-2-carboxylic acid amides according to the invention of the general formula I and corresponding stereoisomers may optionally, like the corresponding acids, the corresponding bases or salts of these compounds, also be obtained in the form of the solvates thereof, preferably the hydrates thereof.

If the substituted 5-aminomethyl-1H-pyrrole-2-carboxylic acid amides according to the invention of the general formula I are obtained after the production thereof in the form of the stereoisomers thereof, preferably in the form of the racemates thereof or other mixtures of their various enantiomers and/or diastereomers, these may be separated and optionally isolated by conventional methods known to the person skilled in the art. Examples which may be mentioned are chromatographic separation processes, in particular liquid chromatography processes at standard pressure or at elevated pressure, preferably MPLC and HPLC processes, and fractional crystallisation processes. Individual enantiomers, e.g. diastereomeric salts formed by means of HPLC on a chiral phase or by means of crystallisation with chiral acids, such as (+)-tartaric acid, (−)-tartaric acid or (+)-10-camphorsulfonic acid, may here in particular be separated from one another.

The substituted 5-aminomethyl-1H-pyrrole-2-carboxylic acid amides according to the invention of the general formula I and corresponding stereoisomers as well as in each case the corresponding acids, bases, salts and solvates are toxicologically safe and are therefore suitable as pharmaceutical active ingredients in pharmaceutical preparations.

The present invention accordingly further provides pharmaceutical preparations containing at least one substituted 5-aminomethyl-1H-pyrrole-2-carboxylic acid amide according to the invention of the general formula I, optionally in the form of the racemate thereof, the pure stereoisomers thereof, in particular enantiomers or diastereomers, or in the form of mixtures of the stereoisomers, in particular the enantiomers, diastereomers or rotamers, in any desired mixing ratio, or in each case in the form of the acids or the bases thereof or in the form of the salts thereof, in particular the physiologically acceptable salts, particularly preferably the hydrochlorides, or in each case in the form of the solvates thereof, in particular the hydrates, and optionally physiologically acceptable auxiliary substances.

These pharmaceutical preparations are in particular suitable for regulating the ORL ("opioid receptor like")-1 receptor, for regulating the μ opioid receptor, for inhibiting noradrenalin uptake and for inhibiting 5-hydroxytryptamine (5-HT) uptake.

The pharmaceutical preparations according to the invention are likewise preferably suitable for combatting pain, preferably for combatting chronic pain and/or acute pain and/or neuropathic pain.

The pharmaceutical preparations according to the invention are furthermore also suitable for the treatment of withdrawal symptoms, memory disorders, neurodegenerative diseases, preferably Parkinson's disease, Huntington's chorea or Alzheimer's disease, epilepsy, disorders of the cardiovascular system, water retention conditions, intestinal motility (diarrhoea), urinary incontinence, anorexia, pruritus, depression, tinnitus, sexual dysfunction, preferably erectile dysfunction, respiratory diseases, or for diuresis, for influencing the cardiovascular system, preferably for vasodilating the arteries, for suppression of the urinary reflex, for anxiolysis, for regulating the electrolyte balance, for regulating, preferably stimulating, food intake, for reducing the addictive potential of opioids, in particular of morphine, for modulating locomotor activity, for influencing the action of μ agonists, in particular morphine.

The present invention also provides the use of one or more substituted 5-aminomethyl-1H-pyrrole-2-carboxylic acid amides of the general formula I, optionally in the form of the pure stereoisomers thereof, in particular enantiomers or diastereomers, the racemates thereof or in the form of mixtures of the stereoisomers, in particular the enantiomers, diastereomers or rotamers, in any desired mixing ratio, or in each case in the form of the acids or bases thereof or in the form of the salts thereof, in particular the physiologically acceptable salts, particularly preferably the hydrochlorides, or in each case in the form of the solvates thereof, in particular the hydrates, for the production of a pharmaceutical preparation for regulating the ORL ("opioid receptor like")-1 receptor, for regulating the μ opioid receptor, for inhibiting noradrenalin uptake or for inhibiting 5-hydroxytryptamine (5-HT) uptake.

The present invention also provides the use of one or more substituted 5-aminomethyl-1H-pyrrole-2-carboxylic acid amides of the general formula I, optionally in the form of the pure stereoisomers thereof, in particular enantiomers or diastereomers, the racemates thereof or in the form of mixtures of the stereoisomers, in particular the enantiomers, diastereomers or rotamers, in any desired mixing ratio, or in each case in the form of the acids or bases thereof or in the form of the salts thereof, in particular the physiologically acceptable salts, particularly preferably the hydrochlorides, or in each case in the form of the solvates thereof, in particular the hydrates, for the production of a pharmaceutical preparation for combatting pain, preferably chronic pain and/or acute pain and/or neuropathic pain, for the treatment of withdrawal symptoms, memory disorders, neurodegenerative diseases, preferably Parkinson's disease, Huntington's chorea or Alzheimer's disease, epilepsy, disorders of the cardiovascular system, water retention conditions, intestinal motility (diarrhoea), urinary incontinence, anorexia, pruritus, depression, tinnitus, sexual dysfunction, preferably erectile dysfunction, respiratory diseases, or for diuresis, for the suppression of the urinary reflex, for anxiolysis, for regulating the electrolyte balance, for influencing the cardiovascular system, preferably for vasodilating the arteries, for regulating, preferably stimulating, food intake, for reducing the addictive potential of opioids, in particular of morphine, for modulating locomotor activity or for influencing the action of μ agonists, in particular morphine.

The pharmaceutical preparations according to the invention may be present as liquid, semisolid or solid dosage forms, for example in the form of solutions for injection, drops, succi, syrups, sprays, suspensions, tablets, patches, capsules, transdermal delivery systems, suppositories, ointments, creams, lotions, gels, emulsions, aerosols or in multiparticulate form, for example in the form of pellets or granules, optionally press-moulded into tablets, packaged in capsules or suspended in a liquid, and also be administered as such.

Apart from one or more substituted 5-aminomethyl-1H-pyrrole-2-carboxylic acid amides of the general formula I, optionally in the form of the racemates thereof, the pure stereoisomers thereof, in particular enantiomers or diastereomers, or in the form of mixtures of the stereoisomers, in particular the enantiomers or diastereomers, in any desired mixing ratio, or in each case in the form of the acid thereof or the base thereof or in the form of the salt thereof, in particular a physiologically acceptable salt, or in the form of the solvate thereof, in particular the hydrate, the pharmaceutical preparations according to the invention conventionally contain further physiologically acceptable pharmaceutical auxiliary substances, which are preferably selected from the group consisting of matrix materials, fillers, solvents, diluents, surface-active substances, dyes, preservatives, disintegrants, slip agents, lubricants, aromas and binders.

Selection of the physiologically acceptable auxiliary substances and the quantities thereof which are to be used depends upon whether the pharmaceutical preparation is to be administered orally, subcutaneously, parenterally, intravenously, intraperitoneally, intradermally, intramuscularly, intranasally, buccally, rectally or topically, for example onto infections of the skin, mucous membranes or eyes.

Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration.

Substituted 5-aminomethyl-1H-pyrrole-2-carboxylic acid amides of the general formula I, optionally in the form of the racemates thereof, the pure stereoisomers thereof, in particular enantiomers or diastereomers, or in the form of mixtures of the stereoisomers, in particular the enantiomers or diastereomers, in any desired mixing ratio, or in each case in the form of the acid thereof or the base thereof or in the form of the salt thereof, in particular a physiologically acceptable salt, or in the form of the solvate thereof, in particular the hydrate, in a depot in dissolved form or in a dressing, optionally with the addition of skin penetration promoters, are suitable percutaneous administration preparations.

Orally or percutaneously administrable formulations may also release the particular substituted 5-aminomethyl-1H-pyrrole-2-carboxylic acid amides of the general formula I, optionally in the form of the racemates thereof, the pure stereoisomers thereof, in particular enantiomers or diastereomers, or in the form of mixtures of the stereoisomers, in particular the enantiomers or diastereomers, in any desired mixing ratio, or in each case in the form of the acid thereof or the base thereof or in the form of the salt thereof, in particular a physiologically acceptable salt, or in the form of the solvate thereof, in particular the hydrate, in delayed manner. Production of the pharmaceutical preparations according to the invention proceeds with the assistance of conventional means, devices, methods and processes known to the person skilled in the art, such as are described for example in A. R. Gennaro (ed.), "Remington's Pharmaceutical Sciences", 17th edition, Mack Publishing Company, Easton, Pa. (1985), in particular in part 8, chapters 76 to 93. The corresponding literature description is hereby introduced as a reference and is deemed to be part of the disclosure.

The quantity of the particular substituted 5-aminomethyl-1H-pyrrole-2-carboxylic acid amide of the general formula I to be administered to patients, optionally in the form of the racemate, the pure stereoisomers, in particular enantiomers or diastereomers, or in the form of mixtures of the stereoisomers, in particular the enantiomers or diastereomers, in any desired mixing ratio, or in each case in the form of the acid or base or in the form of the salt, in particular a physiologically acceptable salt, or in each case in the form of the solvate, in particular the hydrate, may vary and is for example dependent on the weight or age of the patient and on the mode of administration, the indication and the severity of the complaint. Conventionally, 0.005 to 500 mg/kg, preferably 0.05 to 5 mg/kg of patient body weight of at least one substituted 5-aminomethyl-1H-pyrrole-2-carboxylic acid amide of the general formula I, optionally in the form of the racemate thereof, the pure stereoisomers thereof, in particular enantiomers or diastereomers, or in the form of mixtures of the stereoisomers, in particular the enantiomers or diastereomers, in any desired mixing ratio, or in each case in the form of the acid thereof or the base thereof or in the form of the salt thereof, in particular a physiologically acceptable salt, or in the form of the solvate thereof, in particular the hydrate, are administered.

For simplicity and illustrative purposes, the principles of the present invention are described by referring to various examples. One of ordinary skill in the art will readily recognize that the same principles are equally applicable to, and can be implemented in other forms, and that any such variation would be within those modifications that do not part from the true spirit and scope of the present invention. The invention is not limited in its application to the details of any particular formulation shown, since the invention is capable of other embodiments. The following examples are provided for illustrative purposes and do not and should not be understood to limit the claims appended hereto. The terminology used herein is for the purpose of description and not of limitation.

Pharmacological Methods:

a) Method for Determining Affinity for the ORL-1 Receptor

The affinity of the particular substituted 5-aminomethyl-1H-pyrrole-2-carboxylic acid amide of the general formula I for the ORL-1 receptor was determined in a receptor binding assay with $^3$H-nociceptin/Orphanin FQ with membranes of recombinant CHO—ORL1 cells, as described by Ardati et al. in Mol. Pharmacol., 51, 1997, pages 816-824. The corresponding literature description is hereby introduced as a reference and is deemed to be part of the disclosure.

The concentration of $^3$H-nociceptin/Orphanin FQ in these tests was 0.5 nM. The binding assays were in each case performed with 20 µg of membrane protein per 200 µl batch in 50 mM Hepes, pH 7.4, 10 mM $MgCl_2$ and 1 mM EDTA. Binding to the ORL1 receptor was determining using 1 mg portions of WGA-SPA Beads (Amersham-Pharmacia, Freiburg, Germany), by one hour's incubation of the batch at room temperature (approx. 20-25° C.) and subsequent measurement in a Trilux scintillation counter (Wallac, Finland).

b) Method for Determining Affinity for the Human µ Opiate Receptor

Receptor affinity for the human µ opiate receptor was determined in a homogeneous batch in microtitre plates. To this end, dilution series of the particular substituted 5-aminomethyl-1H-pyrrole-2-carboxylic acid amide of the general formula I to be tested were incubated at room temperature for 90 minutes in a total volume of 250 µl with a receptor membrane preparation (15-40 µg of protein per 250 µl of incubation batch) of CHO—K1 cells, which express the human µ opiate receptor (RB—HOM receptor membrane preparation from NEN, Zaventem, Belgium) in the presence of 1 nmol/l of the radioactive ligand [$^3$H]-naloxone (NET719, from NEN, Zaventem, Belgium) and of 1 mg of WGA-SPA beads (wheat germ agglutinin SPA beads from Amersham/Pharmacia, Freiburg, Germany). The incubation buffer used was 50 mmol/l tris-HCl supplemented with 0.05 wt. % of sodium azide and with 0.06 wt. % of bovine serum albumin. 25 µmol/l of naloxone were additionally added to determine nonspecific binding. Once the ninety minute incubation time had elapsed, the microtitre plates were centrifuged off for 20 minutes at 1000 g and the radioactivity measured in a β-Counter (Microbeta-Trilux, from PerkinElmer Wallac, Freiburg, Germany). The percentage displacement of the radioactive ligand from its binding to the human µ opiate receptor was determined at a concentration of the compounds to be tested of 1 µmol/l and stated as percentage inhibition of specific binding. On the basis of the percentage displacement by different concentrations of the compounds to be tested of the general formula I, $IC_{50}$ inhibition concentrations which bring about 50% displacement of the radioactive ligand were calculated. $K_i$ values for the test substances were obtained by conversion using the Cheng-Prusoff equation.

c) Method for Determining Noradrenalin and the 5-HT Uptake Inhibition:

Synaptosomes from rat brain regions (the "P2" fraction was used) were freshly isolated for in vitro studies, as described in the publication "The isolation of nerve endings from brain" by E. G. Gray and V. P. Whittaker, J. Anatomy 76, pages 79-88, 1962. The corresponding literature description is hereby introduced as a reference and is deemed to be part of the disclosure.

The tissue (hypothalamus for the determination of noradrenalin uptake inhibition and medulla and pons for the determination of 5-HT uptake inhibition) was homogenised in ice-cooled 0.32 M sucrose (100 mg of tissue/1 mL) in a glass homogeniser with teflon pestle using five complete up and down strokes at 840 revolutions/minute.

The homogenate was centrifuged at 4° C. for 10 minutes at 1000 g. After subsequent centrifugation at 17000 g for 55 minutes, the synaptosomes ($P_2$ fraction) were obtained, which were resuspended in 0.32 M glucose (0.5 mL/100 mg of original weight).

The particular uptake was measured in a 96-well microtitre plate. The volume was 250 µl and the incubation proceeded at room temperature (approx. 20-25° C.) under an $O_2$ atmosphere.

The incubation time was 7.5 minutes for [$^3$H]-NA and 5 minutes for [$^3$H]-5-HT. The 96 samples were then filtered through a Unifilter GF/B® microtitre plate (Packard) and washed with 200 ml of incubated buffer using a "Brabdel MPXRI-96T Cell-Harvester". The Unifilter GF/B plate was dried for 1 hour at 55° C. The plate was then sealed with a Back seal® (Packard) and 35 µl of scintillation fluid were added per well (Ultima gold®, Packard). After sealing with a top seal® (Packard) and establishment of equilibrium (around 5 hours), radioactivity was determined in a "Trilux 1450 Microbeta" (Wallac).

The following characteristics were determined for the NA transporter:

NAuptake: Km=0.32±0.11 µM

The quantity of protein used in the above determination corresponded to the values known from the literature, as for example described in "Protein measurement with the folin phenol reagent", Lowry et al., J. Biol. Chem., 193, 265-275, 1951. A detailed description of the method may also be found in the literature, for example in M.Ch. Frink, H.-H. Hennies, W. Engelberger, M. Haurand and B. Wilffert (1996) Arzneim.-Forsch./Drug Res. 46 (III), 11, 1029-1036. The corresponding literature descriptions are hereby introduced as a reference and are deemed to be part of the disclosure.

d) Investigation of Analgesic Efficacy by the Writhing Test

Investigation of the compounds according to the invention of the general formula I for analgesic efficacy was performed by phenylquinone-induced writhing in the mouse, modified after I. C. Hendershot and J. Forsaith (1959) J. Pharmacol. Exp. There. 125. 237-240. The corresponding literature description is hereby introduced as a reference and is deemed to be part of the disclosure.

Male NMRI mice weighing from 25 to 30 g were used for this purpose. Groups of 10 animals per substance dose received, 10 minutes after intravenous administration of the compounds to be tested, 0.3 ml/mouse of a 0.02% aqueous solution of phenylquinone (phenylbenzoquinone, Sigma, Deisenhofen, Germany; solution prepared with addition of 5% of ethanol and stored in a water bath at 45° C.) administered intraperitoneally. The animals were placed individually in observation cages. A push button counter was used to record the number of pain-induced stretching movements (writhing reactions=straightening of the torso with stretching of the rear extremities) for 5-20 minutes after phenylquinone administration. The control was provided by animals which had received only physiological common salt solution. All the compounds were tested at the standard dosage of 10 mg/kg.

The invention is explained below with reference to Examples. These explanations are given merely by way of example and do not restrict the general concept of the invention.

EXAMPLES

The NMR spectra were measured on a Bruker DPX 300 instrument for the 300 MHz spectra and on a Bruker DRX 600 instrument for the 600 MHz spectra.

The particular chemicals and solvents were purchased from the conventional manufacturers.

A) General Synthesis Method for the Production of Compounds of the General Formula II:

The particular pyrrole-2-carboxylic acid (50 mmol) of the general formula IV was suspended in 200 ml of toluene. Then, with cooling in an ice bath, 100 mmol of sodium hydride (NaH) were slowly added and the mixture stirred for approx. 10 minutes at room temperature.

After addition of 200 mmol of oxalyl chloride, the reaction mixture was refluxed for 15 minutes and then the excess oxalyl chloride and the solvent were removed in a rotary evaporator.

The resultant residue was redissolved in 200 ml of diethyl ether, slowly combined with 100 mmol of the corresponding amine and the resultant reaction mixture was refluxed for two hours. After cooling, the reaction mixture was washed three times with 50 ml portions of water. The organic phase was separated, dried with magnesium sulfate and evaporated in a rotary evaporator. The resultant crude product was used without further purification in the following synthesis steps.

The compounds of the general formula II produced by the above general synthesis method are listed in Table 1 below:

TABLE 1

| Compound | $R^4$ | $R^5$ | $R^6$ |
|---|---|---|---|
| II-1 | —$(CH_2)_2$—O—$(CH_2)_2$— | | $CH_3$ |
| II-2 | N-methylpiperazinyl | | $CH_3$ |
| II-3 | N-phenylpiperazinyl | | $CH_3$ |
| II-4 | —$(CH_2)_5$— | | $CH_3$ |
| II-5 | —$(CH_2)_4$— | | $CH_3$ |
| II-6 | $(CH_2)_2$phenyl | H | $CH_3$ |
| II-7 | $CH_2$phenyl | $CH_3$ | $CH_3$ |
| II-8 | $CH_2$phenyl | $CH(CH_3)_2$ | $CH_3$ |
| II-9 | $CH_2$phenyl | $CH_2$phenyl | $CH_3$ |
| II-10 | $CH_2$-2-pyridine | H | $CH_3$ |
| II-11 | $CH_2$-3-pyridine | H | $CH_3$ |
| II-12 | $CH_2$-4-fluorophenyl | H | $CH_3$ |
| II-13 | $CH_2$-2-furyl | H | $CH_3$ |
| II-14 | $CH_2$-2-methoxyphenyl | H | $CH_3$ |
| II-15 | $(CH_2)_2$-4-methoxyphenyl | H | $CH_3$ |
| II-16 | $(CH_2)_2$-3,4-dimethoxyphenyl | H | $CH_3$ |
| II-17 | cyclopropyl | H | $CH_3$ |
| II-18 | cyclohexyl | H | $CH_3$ |
| II-19 | cyclohexyl | $CH_3$ | $CH_3$ |
| II-20 | cyclohexyl | cyclohexyl | $CH_3$ |
| II-21 | cyclooctyl | H | $CH_3$ |
| II-22 | $(CH_2)_3CH_3$ | H | $CH_3$ |
| II-23 | $(CH_2)_3CH_3$ | $CH_3$ | $CH_3$ |
| II-24 | $(CH_2)_2$-morpholino | H | $CH_3$ |
| II-25 | $(CH_2)_3$-morpholino | H | $CH_3$ |

The structure of the compounds II-1 to II-25 was in each case determined by means of $^1$H-NMR spectroscopy. The chemical shifts of selected compounds are shown below.

II-1)

(1-Methyl-1H-pyrrol-2-yl)-morpholin-4-yl-methanone

δ (DMSO, 300 MHz)=3.58-3.66 (m, 8 H, N($CH_2CH_2)_2$O, N($CH_2CH_2)_2$O); 3.69 (s, 3 H, $NCH_3$); 5.98-6.05 (m, 1 H, N($CH_3$)]—CHCHCHC—[); 6.24-6.32 (m, 1 H, N($CH_3$)]—CHCHCHC—[); 6.78-6.88 (m, 1 H, N($CH_3$)]—CHCHCHC—[).

II-2)

(4-Methylpiperazin-1-yl)-(1-methyl-1H-pyrrol-2-yl)-methanone

δ (DMSO, 300 MHz)=2.21 (s, 3 H, N—$CH_3$); 2.28-2.39 (m, 4 H, N($CH_2CH_2)_2$NMe); 3.57-3.64 (m, 4 H, N($CH_2CH_2)_2$NMe); 3.66 (s, 3 H, $NCH_3$); 6.01 (dd, 1 H, J=3.7 Hz, J=1.5 Hz, N($CH_3$)]—CHCHCHC—[); 6.26 (dd, 1 H, J=1.5 Hz, J=4.5 Hz, N($CH_3$)]—CHCHCHC—[); 6.82-6.85 (m, 1 H, N($CH_3$)—]—CHCHCHC—[).

II-3)

(1-Methyl-1H-pyrrol-2-yl)-(4-phenyl-piperazin-1-yl)-methanone

δ (DMSO, 300 MHz)=3.13-3.23 (m, 4 H, N($CH_2CH_2)_2$NPh); 3.70 (s, 3 H, $NCH_3$); 3.73-3.83 (m, 4 H, N($CH_2CH_2)_2$NPh); 6.04 (dd, 1 H, J=2.6 Hz, J=3.7 Hz, N($CH_3$)]—CHCHCHC—[); 6.34 (dd, 1 H, J=1.5 Hz, J=3.7 Hz, N($CH_3$)]—CHCHCHC—[); 6.77-6.89 (m, 2 H, N($CH_3$)]—CHCHCHC—[, Ph); 6.91-6.99 (m, 2 H, Ph); 7.17-7.28 (m, 2 H, Ph).

II-4)

(1-Methyl-1H-pyrrol-2-yl)-piperidin-1-yl-methanone

δ (DMSO, 300 MHz)=1.45-1.68 (m, 6 H, N—[($CH_2)_2$—$CH_2$—($CH_2)_2$—[); 3.51-3.62 (m, 4 H, N—[($CH_2)_2$—$CH_2$—($CH_2M$); 3.65 (s, 3 H, $NCH_3$); 5.97-6.03 (m, 1 H, N($CH_3$)—]—CHCHCHC—[); 6.21-6.25 (m, 1 H, N($CH_3$)]—CHCHCHC—[); 6.79-6.84 (m, 1 H, N($CH_3$)]—CHCHCHC—[).

II-6)

1-Methyl-1H-pyrrole-2-carboxylic acid phenethylamide

δ (DMSO, 300 MHz)=2.73-2.88 (m, 2 H, $CH_2CH_2$Ph); 3.34-3.48 (m, 2 H, $CH_2CH_2$Ph); 3.84 (s, 3 H, $NCH_3$); 5.92-6.01 (m, 1 H, N($CH_3$)]—CHCHCHC—[); 6.65-6.75 (m, 1 H, N($CH_3$)—]—CHCHCHC—[); 6.75-6.84 (m, 1 H, N($CH_3$)—]—CHCHCHC—[);
7.10-7.36 (m, 5 H, Ph); 7.95-8.08 (m, 1 H, NH).

II-7)

1-Methyl-1H-pyrrole-2-carboxylic acid benzylmethylamide

δ (DMSO, 300 MHz)=2.99 (br. s, 3 H, $NCH_3$Bn); 3.71 (s, 3 H, $NCH_3$); 4.65-4.75 (m, 2 H, $CH_2$Ph); 5.96-6.04 (m, 1 H, N($CH_3$)]—CHCHCHC—[); 6.28-6.41 (m, 1 H, N($CH_3$)—]—CHCHCHC—[); 6.87-6.93 (m, 1 H, N($CH_3$)—]—CHCHCHC—[); 7.18-7.43 (m, 5 H, Ph).

II-8)

1-Methyl-1H-pyrrole-2-carboxylic acid benzylisopropylamide

δ (DMSO, 300 MHz)=1.15 (d, 3 H, J=6.8 Hz, $CH(CH_3)_2$); 3.67 (s, 3 H, $NCH_3$); 4.52-4.67 (m, 3 H, $CH_2$Ph, $CH(CH_3)_2$); 5.95-6.03 (m, 1 H, N($CH_3$)]—CHCHCHC—[); 6.25-6.34 (m, 1 H, N($CH_3$)—]—CHCHCHC—[); 6.80-6.86 (m, 1 H, N($CH_3$)—]—CHCHCHC—[);
7.15-7.36 (m, 5 H, Ph).

II-9)

1-Methyl-1H-pyrrole-2-carboxylic acid dibenzylamide

δ (DMSO, 300 MHz)=3.73 (s, 3 H, $NCH_3$); 4.58-4.72 (m, 4 H, $CH_2$Ph); 5.95 (dd, 1 H, J=2.6 Hz, J=6.0 Hz, N($CH_3$)]—CHCHCHC—[); 6.23-6.29 (m, 1 H, N($CH_3$)—)—CHCHCHC—[); 6.88-6.93 (m, 1 H, N($CH_3$)—]—CHCHCHC—[); 7.16-7.42 (m, 10 H, Ph).

II-10)

1-Methyl-1H-pyrrole-2-carboxylic acid (pyridin-2-ylmethyl)-amide

δ (DMSO, 300 MHz)=3.85 (s, 3 H, $NCH_3$); 4.49 (d, 2 H, J=6.0 Hz, $CH_2$pyridine); 5.99-6.04 (m, 1 H, N($CH_3$)]—CHCHCHC—[); 6.83-6.89 (m, 2 H, N($CH_3$)—]—CHCHCHC—[); 7.18-7.25 (m, 1 H, pyridine); 7.30 (d, 1 H, J=7.9

Hz, pyridine); 7.72 (dt, 1 H, J=1.9 Hz, J=7.5 Hz, pyridine); 8.46-8.52 (m, 1 H, pyridine); 8.52-8.59 (m, 1 H, NH).

II-11)

1-Methyl-1H-pyrrole-2-carboxylic acid (pyridin-3-ylmethyl)-amide

δ (DMSO, 300 MHz)=3.85 (s, 3 H, NCH$_3$); 4.42 (d, 2 H, J=6.0 Hz, CH$_2$pyridine); 5.98-6.02 (m, 1 H, N(CH$_3$)]—CHCHCHC—[); 6.80-6.85 (m, 1 H, N(CH$_3$)—]—CHCH-CHC—[); 6.85-6.88 (m, 1 H, N(CH$_3$)—]—CHCHCHC—[); 7.32 (dd, 1 H, J=4.9 Hz, J=7.5 Hz, pyridine); 7.65-7.71 (m, 1 H, pyridine); 8.42-8.45 (m, 1 H, pyridine); 8.51-8.58 (m, 2 H, pyridine, NH).

II-12)

1-Methyl-1H-pyrrole-2-carboxylic acid 4-fluoro-benzylamide

δ (DMSO, 300 MHz)=3.84 (s, 3 H, NCH$_3$); 4.37 (d, 2 H, J=6.0 Hz, CH$_2$4-FPh); 5.98-6.03 (m, 2 H, N(CH$_3$)]—CHCHCHC—[); 6.88-6.90 (m, 1 H, N(CH$_3$)]—CHCH-CHC—[); 7.09-7.17 (m, 2 H, 4-FPh); 7.28-7.36 (m, 2 H, 4-FPh); 8.47-8.58 (m, 1 H, NH).

II-13)

1-Methyl-1H-pyrrole-2-carboxylic acid (furan-2-ylmethyl)-amide

δ (DMSO, 300 MHz)=3.85 (s, 3 H, NCH$_3$); 4.38 (d, 2 H, J=5.7 Hz, CONHCH$_2$); 5.95-6.03 (m, 1 H, O]—CHCH-CHC—[); 6.19-6.26 (m, 1 H, N(CH$_3$)]—CHCHCHC—[); 6.34-6.40 (m, 1 H, O]—CHCHCHC—[); 6.78-6.84 (m, 1 H, N(CH$_3$)]—CHCHCHC—[); 6.85-6.90 (m, 1 H, N(CH$_3$)]—CHCHCHC—[); 7.49-7.56 (m, 1 H, O]—CHCHCHC—[); 8.36-8.46 (m, 1 H, NH).

II-14)

1-Methyl-1H-pyrrole-2-carboxylic acid 2-methoxy-benzylamide

δ (DMSO, 300 MHz)=3.83 (s, 3 H, NCH$_3$); 3.85 (s, 3 H, OCH$_3$); 4.38 (d, 2 H, J=6.0 Hz, CH$_2$-o-OMePh); 5.96-6.03 (m, 1 H, N(CH$_3$)]—CHCHCHC—[); 6.81-7.00 (m, 4 H, N(CH$_3$)]—CHCHCHC—[, p-OMePh); 7.13-7.27 (m, 2 H, p-OMePh); 8.22-8.32 (m, 1 H, NH).

II-15)

1-Methyl-1H-pyrrole-2-carboxylic acid [2-(4-methoxyphenyl)-ethyl]-amide

δ (DMSO, 300 MHz)=2.72 (d, 1 H, J=7.1 Hz, CH$_2$CH$_2$-p-OMePh); 2.75 (d, 1 H, J=7.9 Hz, CH$_2$CH$_2$-p-OMePh); 3.27-3.41 (m, 2 H, CH$_2$CH$_2$-p-OMePh); 3.72 (s, 3 H, NCH$_3$); 3.83 (s, 3 H, OCH$_3$); 5.93-6.01 (m, 1 H, N(CH$_3$)]—CHCHCHC—[); 6.66-6.73 (m, 1 H, N(CH$_3$)—]—CHCH-CHC—[); 6.78-6.88 (m, 3 H, N(CH$_3$)]—CHCHCHC—[, p-OMePh); 7.13 (d, 2 H, J=8.7 Hz, -[, p-OMePh); 7.95-8.02 (m, 1 H, NH).

II-16)

1-Methyl-1H-pyrrole-2-carboxylic acid [2-(3,4-dimethoxyphenyl)-ethyl]-amide

δ (DMSO, 300 MHz)=2.73 (d, 1 H, J=7.5 Hz, CH$_2$CH$_2$(3,4-(OMe)$_2$Ph); 2.75 (d, 1 H, J=7.5 Hz, CH$_2$CH$_2$(3,4-(OMe)$_2$Ph); 3.34-3.45 (m, 2 H, CH$_2$CH$_2$(3,4-(OMe)$_2$Ph); 3.73 (s, 3 H, NCH$_3$); 5.97 (dd, 1 H, J=2.6 Hz, J=3.0 Hz N(CH$_3$)]—CHCHCHC—[); 6.70-6.75 (m, 2 H, N(CH$_3$)]—CHCHCHC—[); 6.80-6.85 (m, 3 H, (3,4-(OMe)$_2$Ph); 7.91-8.01 (m, 1 H, NH).

II-17)

1-Methyl-1H-pyrrole-2-carboxylic acid cyclopropylamide

δ (DMSO, 300 MHz)=0.47-0.68 (m, 4 H,]—CH$_2$CHCH$_2$—[); 2.68-2.78 (m, 1 H,]—CH$_2$CHCH$_2$—[); 3.84 (s, 3 H, NCH$_3$); 5.91-5.99 (m, 1 H, N(CH$_3$)—]—CHCHCHC—[); 6.68-6.75 (m, 1 H, N(CH$_3$)]—CHCH-CHC—[); 6.77-6.84 (m, 1 H, N(CH$_3$)]—CHCHCHC—[); 7.89 (br. s, 1 H, NH).

II-18)

1-Methyl-1H-pyrrole-2-carboxylic acid cyclohexylamide 1.02-1.39 (m, 6 H, NH]—CH(CH$_2$)$_2$(CH$_2$)$_2$CH$_2$—[); 1.54-1.88 (m, 4 H, NH]—CH(CH$_2$)$_2$(CH$_2$)$_2$CH$_2$—[); 3.60-3.78 (m, 1 H, NH]—CH(CH$_2$)$_2$(CH$_2$)$_2$CH$_2$—[); 3.83 (s, 3 H, NCH$_3$); 5.92-6.00 (m, 1 H, N(CH$_3$)]—CHCHCHC—[); 6.69-6.87 (m, 2 H, N(CH$_3$)]—CHCHCHC—[); 7.51-7.66 (m, 1 H, NH).

II-19)

1-Methyl-1H-pyrrole-2-carboxylic acid cyclohexylmethylamide

δ (DMSO, 300 MHz)=0.88-1.36 (m, 4 H, N]—CH(CH$_2$)$_2$(CH$_2$)$_2$CH$_2$—[); 1.44-1.85 (m, 6 H, N]—CH(CH$_2$)$_2$(CH$_2$)$_2$CH$_2$—[); 2.88 (s, 3 H, N—CH$_3$); 3.64 (s, 3 H, NCH$_3$); 4.03-4.19 (m, 1 H, N]—CH(CH$_2$)$_2$(CH$_2$)$_2$CH$_2$—[); 5.97-6.04 (m, 1 H, N(CH$_3$)]—CHCHCHC—[); 6.19-6.29 (m, 1 H, N(CH$_3$)]—CHCHCHC—[); 6.79-6.85 (m, 1 H, N(CH$_3$)]—CHCHCHC—[).

II-20)

1-Methyl-1H-pyrrole-2-carboxylic acid dicyclohexylamide

δ (DMSO, 300 MHz)=1.03-1.33 (m, 6 H, N]—CH(CH$_2$)$_2$(CH$_2$)$_2$CH$_2$—[); 1.49-1.83 (m, 11 H, N]—CH(CH$_2$)$_2$(CH$_2$)$_2$CH$_2$—[); 1.84-2.14 (m, 3 H, N]—CH(CH$_2$)$_2$(CH$_2$)$_2$CH$_2$—[); 3.38-3.55 (m, 2 H, N]—CH(CH$_2$)$_2$(CH$_2$)$_2$CH$_2$—[); 3.64 (s, 3 H, NCH$_3$); 5.93-6.00 (m, 1 H, N(CH$_3$)]—CHCHCHC—[); 6.03-6.11 (m, 1 H, N(CH$_3$)]—CHCHCHC—[); 6.73-6.80 (m, 1 H, N(CH$_3$)]—CHCH-CHC—[).

II-21)

1-Methyl-1H-pyrrole-2-carboxylic acid cyclooctylamide

δ (DMSO, 300 MHz)=1.38-1.77 (m, 16 H, NCH(CH$_2$)$_7$); 3.82 (s, 3 H, NCH$_3$); 3.88-4.02 (m, 1 H, NCH(CH$_2$)$_7$);

5.93-5.99 (m, 1 H, N(CH$_3$)]—CHCHCHC—[); 6.75-6.83 (m, 2 H, N(CH$_3$)—]—CHCHCHC—[); 7.68-7.59 (m, 1 H, NH).

II-22)

1-Methyl-1H-pyrrole-2-carboxylic acid butylamide

δ (DMSO, 300 MHz)=0.90 (t, 3 H, J=7.2 Hz, CH$_3$CH$_2$CH$_2$CH$_2$); 1.21-1.40 (m, 2 H, CH$_3$CH$_2$CH$_2$CH$_2$); 1.40-1.56 (m, 2 H, CH$_3$CH$_2$CH$_2$CH$_2$); 3.17 (dd, 2 H, J=6.4 Hz, J=13.5 Hz, CH$_3$CH$_2$CH$_2$CH$_2$); 3.83 (s, 3 H, NCH$_3$); 5.93 (m, 1 H, N(CH$_3$)—]—CHCHCHC—[); 6.68-6.75 (m, 1 H, N(CH$_3$)]—CHCHCHC—[); 6.76-6.83 (m, 1 H, N(CH$_3$)]—CHCHCHC—[); 7.78-7.93 (m, 1 H, NH).

II-23)

1-Methyl-1H-pyrrole-2-carboxylic acid butylmethylamide

δ (DMSO, 300 MHz)=0.88 (t, 3 H, J=7.2 Hz, CH$_3$CH$_2$CH$_2$CH$_2$); 1.18-1.34 (m, 2 H, CH$_3$CH$_2$CH$_2$CH$_2$); 1.47-1.61 (m, 2 H, CH$_3$CH$_2$CH$_2$CH$_2$); 3.01 (br. s, 3 H, NCH$_3$); 3.44 (t, 2 H, J=7.2 Hz, CH$_3$CH$_2$CH$_2$CH$_2$); 3.65 (s, 3 H, NCH$_3$); 5.97-6.03 (m, 1 H, N(CH$_3$)—]—CHCH-CHC—[); 6.25-6.32 (m, 1 H, N(CH$_3$)]—CHCHCHC—[); 6.81-6.83 (m, 1 H, N(CH$_3$)]—CHCHCHC—[).

II-24)

1-Methyl-1H-pyrrole-2-carboxylic acid (3-morpholin-4-yl-ethyl)-amide

δ (DMSO, 300 MHz)=2.38-2.45 (m, 6 H, CONHCH$_2$CH$_2$, N(CH$_2$CH$_2$)$_2$O); 3.27-3.34 (m, 2 H, CONHCH$_2$CH$_2$); 3.54-3.62 (m, 4 H, N(CH$_2$CH$_2$)$_2$O); 3.83 (s, 3 H, NCH$_3$); 5.98 (dd, 1 H, J=2.6 Hz, J=3.7 Hz, N(CH$_3$)]—CHCHCHC—[); 6.69-6.71 (m, 1 H, N(CH$_3$)]—CHCHCHC—[); 6.80-6.84 (m, 1 H, N(CH$_3$)—]—CHCH-CHC—[); 7.77-7.84 (m, 1 H, NH).

II-25)

1-Methyl-1H-pyrrole-2-carboxylic acid (3-morpholin-4-yl-propyl)-amide

δ (DMSO, 300 MHz)=1.58-1.68 (m, 2 H, CONHCH$_2$CH$_2$CH$_2$); 2.23-2.42 (m, 6 H, CONHCH$_2$CH$_2$CH$_2$, N(CH$_2$CH$_2$)$_2$O); 3.17 (d, 1 H, J=6.8 Hz, CONHCH$_2$CH$_2$CH$_2$); 3.21 (d, 1 H, J=6.8 Hz, CONHCH$_2$CH$_2$CH$_2$); 3.35-3.60 (m, 4 H, N(CH$_2$CH$_2$)$_2$O); 3.81 (s, 3 H, NCH$_3$); 5.96-6.03 (m, 1 H, N(CH$_3$)]—CHCH-CHC—[); 6.67-6.76 (m, 1 H, N(CH$_3$)—]—CHCHCHC—[); 6.83-6.91 (m, 1 H, N(CH$_3$)—]—CHCHCHC—[); 7.90-8.03 (m, 1 H, NH).

B)

General Synthesis Method for the Production of Compounds of the General Formula III:

A solution of one equivalent of acetyl chloride in diethyl ether was slowly added dropwise with stirring to the ice-cooled solution or suspension of one equivalent of the particular compound of the general formula V. Stirring of the reaction mixture was then continued for one hour at room temperature. A precipitate formed, which was removed by suction filtration under nitrogen and then dried under an oil pump vacuum. The resultant iminium salts of the general formula III were then used in the following synthesis step without any further purification.

At variance with this synthesis method, compounds III-4 and III-5 were not isolated, but instead directly used in the following synthesis step.

The compounds of the general formula III produced by the above general synthesis method are shown in Table 2 below:

TABLE 2

| Compound | R$^1$ | R* | R$^3$ |
|---|---|---|---|
| III-1 | CH$_3$ | CH$_3$ | 4-fluorophenyl |
| III-2 | CH$_3$ | CH$_3$ | 4-bromophenyl |
| III-3 | CH$_3$ | CH$_3$ | phenyl |
| III-4 | CH$_3$ | CH$_3$ | COOC$_2$H$_5$ |
| III-5 | —(CH$_2$)$_5$— | | COOC$_2$H$_5$ |

C)

General Synthesis Method for the Production of Compounds According to the Invention According to Examples 1-15:

The particular compounds of the general formulae II and III were dissolved in acetonitrile or compounds III-4 and III-5 were used directly as obtained according to B) and stirred overnight at room temperature (approx. 20-25° C.). The resultant solution was first acidified with aqueous hydrochloric acid and nonbasic impurities were extracted with diethyl ether. The aqueous phase was then combined with Na$_2$CO$_3$ solution and the particular example compound extracted with diethyl ether. The resultant ethereal solution was dried over magnesium sulfate. The particular compound according to the invention of Examples 1-15 was then converted with the assistance of an ethanolic hydrogen chloride solution into the corresponding hydrochloride and isolated by filtration. The resultant salt was then purified by washing with ethanol.

The particular compounds of the general formulae II and III used for the production of example compounds according to the invention are shown in Table 3 below.

TABLE 3

| Example | Compound of the general formula II used | Compound of the general formula III used |
|---|---|---|
| 1 | II-18 | III-1 |
| 2 | II-22 | III-1 |
| 3 | II-5 | III-1 |
| 4 | II-18 | III-2 |
| 5 | II-22 | III-2 |
| 6 | II-5 | III-2 |
| 7 | II-6 | III-2 |
| 8 | II-1 | III-2 |
| 9 | II-18 | III-3 |
| 10 | II-22 | III-3 |
| 11 | II-5 | III-3 |
| 12 | II-22 | III-4 |
| 13 | II-18 | III-4 |
| 14 | II-22 | III-5 |
| 15 | II-18 | III-5 |

The structure of the example compounds according to the invention was in each case determined by $^1$H-NMR spectroscopy. The values obtained are in each case shown

Example 1

5-[Dimethylamino-(4-fluoro-phenyl)-methyl]-1-methyl-1H-pyrrole-2-carboxylic acid cyclohexylamide hydrochloride $^1$H-NMR reveals two rotamers in the ratio of approx. 3:1. Only the signals for the compound in excess are stated.

δ (DMSO, 600 MHz)=1.05-1.15 (m, 1 H, NH]—CH(CH$_2$)$_2$(CH$_2$)$_2$CH$_2$—[); 1.18-1.32 (m, 5 H, NH]—CH(CH$_2$)$_2$(CH$_2$)$_2$CH$_2$—[); 1.65-1.85 (m, 4 H, NH]—CH(CH$_2$)$_2$(CH$_2$)$_2$CH$_2$); 2.61(d, 3 H, J=4.5 Hz, N(CH$_3$)$_2$); 2.79 (d, 3 H, J=4.5 Hz, N(CH$_3$)$_2$); 3.60-3.72 (m, 1 H, NH]—CH(CH$_2$)$_2$(CH$_2$)$_2$CH$_2$—[); 3.84 (s, 3 H, NCH$_3$); 5.82 (d, 1 H, J=9.1 Hz, CHN(CH$_3$)$_2$); 6.81 (d, 1 H, J=3.8 Hz, N(CH$_3$)]—CCHCHC—[); 6.86 (d, 1 H, J=3.8 Hz, N(CH$_3$)]—CCHCHC—]); 7.24-7.34 (m, 2 H, p-FPh); 7.72-7.82 (m, 3 H, p-FPh, NH); 11.64(3.1 H, HCl).

Example 2

5-[Dimethylamino-(4-fluoro-phenyl)-methyl]-1-methyl-1H-pyrrole-2-carboxylic acid butylamide hydrochloride $^1$H-NMR reveals two rotamers in the ratio of approx. 3:1. Only the signals for the compound in excess are stated.

δ (DMSO, 600 MHz)=0.88 (t, 3 H, J=7.5 Hz, CH$_3$CH$_2$CH$_2$CH$_2$); 1.25-1.34 (m, 2 H, CH$_3$CH$_2$CH$_2$CH$_2$); 1.40-1.48 (m, 2 H, CH$_3$CH$_2$CH$_2$CH$_2$); 2.61 (d, 3 H, J=4.5 Hz, N(CH$_3$)$_2$); 2.79 (d, 3 H, J=4.5 Hz, N(CH$_3$)$_2$); 3.10-3.20 (m, 2 H, CH$_3$CH$_2$CH$_2$CH$_2$); 3.86 (s, 3 H, NCH$_3$); 5.85 (d, 1 H, J=9.1 Hz, CHN(CH$_3$)$_2$); 6.79 (d, 1 H, J=3.8 Hz, N(CH$_3$)]—CCHCHC—[); 6.91 (d, 1 H, J=3.8 Hz, N(CH$_3$)]—CCHCHC—[); 7.24-7.32 (m, 2 H, p-FPh); 7.75-7.83 (m, 2 H, p-FPh); 8.03-8.07 (m, 1 H, NH); 11.76 (s, 1 H, HCl).

Example 3

{5-[Dimethylamino-(4-fluoro-phenyl)-methyl]-1-methyl-1H-pyrrol-2-yl}-pyrrolidin-1-yl-methanone hydrochloride $^1$H-NMR reveals two rotamers in the ratio of approx. 4:1. Only the signals for the compound in excess are stated.

δ (DMSO, 600 MHz)=1.72-1.91 (m, 4 H, N(CH$_2$)$_2$(CH$_2$)$_2$); 2.61 (d, 3 H, J=4.5 Hz, N(CH$_3$)$_2$); 2.79 (d, 3 H, J=4.5 Hz, N(CH$_3$)$_2$); 3.35-3.59 (m, 4 H, N(CH$_2$)$_2$(CH$_2$)$_2$); 3.71 (s, 3 H, NCH$_3$); 5.87 (d, 1 H, J=9.1 Hz, CHN(CH$_3$)$_2$); 6.57 (d, 1 H, J=3.8 Hz, N(CH$_3$)]—CCHCHC—[); 6.95 (d, 1 H, J=3.8 Hz, N(CH$_3$)]—CCHCHC—[); 7.27-7.33 (m, 2 H, p-FPh); 7.78-7.88 (m, 2 H, p-FPh); 11.85 (s, 1 H, HCl).

Example 4

5-[Dimethylamino-(4-bromo-phenyl)-methyl]-1-methyl-1H-pyrrole-2-carboxylic acid cyclohexylamide hydrochloride $^1$H-NMR reveals two rotamers in the ratio of approx. 4.5:1. Only the signals for the compound in excess are stated.

δ (DMSO, 600 MHz)=1.08-1.16 (m, 1 H, NH]—CH(CH$_2$)$_2$(CH$_2$)$_2$CH$_2$—[); 1.19-1.34 (m, 5 H, NH]—CH(CH$_2$)$_2$(CH$_2$)$_2$CH$_2$—[); 1.53-1.64 (m, 1 H, NH]—CH(CH$_2$)$_2$(CH$_2$)$_2$CH$_2$); 1.65-1.82 (m, 3 H, NH]—CH(CH$_2$)$_2$(CH$_2$)$_2$CH$_2$); 2.63 (d, 3 H, J=4.5 Hz, N(CH$_3$)$_2$); 2.78 (d, 3 H, J=4.5 Hz, N(CH$_3$)$_2$); 3.64-3.72 (m, 1 H, NH]—CH(CH$_2$)$_2$(CH$_2$)$_2$CH$_2$—[); 3.85 (s, 3 H, NCH$_3$); 5.84 (d, 1 H, J=9.1 Hz, CHN(CH$_3$)$_2$); 6.81 (d, 1 H, J=4.5 Hz, N(CH$_3$)]—CCHCHC—[); 6.87 (d, 1 H, J=4.5 Hz, N(CH$_3$)]—CCHCHC—[); 7.63-7.67 (m, 2 H, p-BrPh); 7.67-7.72 (m, 2 H, p-BrPh); 7.81 (d, 1 H, J=8.3 Hz, NH); 11.81 (s, 1 H, HCl).

Example 5

5-[Dimethylamino-(4-bromo-phenyl)-methyl]-1-methyl-1H-pyrrole-2-carboxylic acid butylamide hydrochloride $^1$H-NMR reveals two rotamers in the ratio of approx. 3:1. Only the signals for the compound in excess are stated.

δ (DMSO, 600 MHz)=0.88 (t, 3 H, J=7.2 Hz, CH$_3$CH$_2$CH$_2$CH$_2$); 1.26-1.33 (m, 2 H, CH$_3$CH$_2$CH$_2$CH$_2$); 1.41-1.48 (m, 2 H, CH$_3$CH$_2$CH$_2$CH$_2$); 2.63 (d, 3 H, J=3.8 Hz, N(CH$_3$)$_2$); 2.78 (d, 3 H, J=4.5 Hz, N(CH$_3$)$_2$); 3.11-3.18 (m, 2 H, CH$_3$CH$_2$CH$_2$CH$_2$); 3.86 (s, 3 H, NCH$_3$); 5.85 (d, 1 H, J=9.1 Hz, CHN(CH$_3$)$_2$); 6.79 (d, 1 H, J=3.8 Hz, N(CH$_3$)]—CCHCHC—[); 6.90 (d, 1 H, J=3.8 Hz, N(CH$_3$)]—CCHCHC—[); 7.64-7.68 (m, 2 H, p-BrPh); 7.68-7.73 (m, 2 H, p-BrPh); 8.03-8.08 (m, 1 H, NH); 11.86 (s, 1 H, HCl).

Example 6

{5-[(4-Bromo-phenyl)-dimethylamino-methyl]-1-methyl-1H-pyrrol-2-yl)-pyrrolidin-1-yl-methanone hydrochloride $^1$H-NMR reveals two rotamers in the ratio of approx. 4:1. Only the signals for the compound in excess are stated.

δ (DMSO, 600 MHz)=1.74-1.92 (m, 4 H, N(CH$_2$)$_2$(CH$_2$)$_2$); 2.63 (d, 3 H, J=4.5 Hz, N(CH$_3$)$_2$); 2.78 (d, 3 H, J=4.5 Hz, N(CH$_3$)$_2$); 3.34-3.59 (m, 4 H, N(CH$_2$)$_2$(CH$_2$)$_2$); 3.71 (s, 3 H, NCH$_3$); 5.82-5.89 (m, 1 H, CHN(CH$_3$)$_2$); 6.56 (d, 1 H, J=3.8 Hz, N(CH$_3$)]—CCHCHC—[); 6.92 (d, 1 H, J=3.8 Hz, N(CH$_3$)]—CCHCHC—[); 7.66 (d, 2 H, J=8.3 Hz, p-BrPh); 7.73 (d, 2 H, J=8.3 Hz, p-FPh); 11.86 (s, 1 H, HCl).

Example 7

5-[(4-Bromo-phenyl)-dimethylamino-methyl]-1-methyl-1H-pyrrole-2-carboxylic acid phenethylamide hydrochloride $^1$H-NMR reveals two rotamers in the ratio of approx. 3:1. Only the signals for the compound in excess are stated.

δ (DMSO, 600 MHz)=2.59-2.61 (m, 2 H, CH$_2$CH$_2$Ph); 2.67-2.71 (m, 2 H, CH$_2$CH$_2$Ph); 2.75-2.79 (m, 6 H, N(CH$_3$)$_2$); 3.85 (s, 3 H, NCH$_3$); 5.82 (d, 1 H, J=9.1 Hz, CHN(CH$_3$)$_2$); 6.77 (d, 1 H, J=3.8 Hz, N(CH$_3$)]—CCHCHC—[); 6.86 (d, 1 H, J=3.8 Hz, N(CH$_3$)]—CCHCHC—[); 7.17-7.31 (m, 7 H, p-BrPh, Ph); 7.63-7.71 (m, 2 H, p-BrPh); 8.19-8.23 (m, 1 H, NH); 11.66 (s, 1 H, HCl).

Example 8

{5-[(4-Bromo-phenyl)-dimethylamino-methyl]-1-methyl-1H-pyrrol-2-yl}-morpholin-4-yl-methanone hydrochloride δ (DMSO, 600 MHz)=2.59-2.69 (m, 4 H, N(CH$_2$CH$_2$)$_2$O); 2.74-2.83 (m, 4 H, N(CH$_2$CH$_2$)$_2$O); 3.51-3.59 (m, 6 H, N(CH$_3$)$_2$); 3.63 (s, 3 H, NCH$_3$); 5.78-5.85 (m, 1 H, CHN(CH$_3$)$_2$); 6.39 (d, 1 H, J=3.8 Hz, N(CH$_3$)]—CCHCHC—[); 6.82 (d, 1 H, J=3.8 Hz, N(CH$_3$)]—CCHCHC—[); 7.65-7.71 (m, 4 H, p-BrPh); 11.44 (s, 1 H, HCl).

Example 9

5-(Dimethylamino-phenyl-methyl)-1-methyl-1H-pyrrole-2-carboxylic acid cyclohexylamide hydrochloride $^1$H-NMR reveals two rotamers in the ratio of approx. 4:1. Only the signals for the compound in excess are stated.

δ (DMSO, 600 MHz)=1.08-1.15 (m, 1 H, NH]—CH(CH$_2$)$_2$(CH$_2$)$_2$CH$_2$—[); 1.21-1.33 (m, 5 H, NH]—CH(CH$_2$)$_2$(CH$_2$)$_2$CH$_2$—[); 1.65-1.85 (m, 4 H, NH]—CH(CH$_2$)$_2$(CH$_2$)$_2$CH$_2$); 2.61 (d, 3 H, J=4.5 Hz, N(CH$_3$)$_2$); 2.78 (d, 3 H, J=4.5 Hz, N(CH$_3$)$_2$); 3.61-3.70 (m, 1 H, NH]—CH(CH$_2$)$_2$(CH$_2$)$_2$CH$_2$—[); 3.86 (s, 3 H, NCH$_3$); 5.80 (d, 1 H, J=9.1 Hz, CHN(CH$_3$)$_2$); 6.81 (d, 1 H, J=4.5 Hz, N(CH$_3$)]—CCHCHC—[); 6.89 (d, 1 H, J=3.8 Hz, N(CH$_3$)]—CCHCHC—[); 7.36-7.41 (m, 1 H, Ph); 7.42-7.49 (m, 2 H, Ph); 7.42-7.49 (m, 2 H, Ph); 7.80 (d, 1 H, J=8.3 Hz, NH); 11.74 (s, 1 H, HCl).

Example 10

5-(Dimethylamino-phenyl-methyl)-1-methyl-1H-pyrrole-2-carboxylic acid butylamide hydrochloride $^1$H-NMR reveals two rotamers in the ratio of approx. 4:1. Only the signals for the compound in excess are stated.

δ (DMSO, 600 MHz)=0.88 (t, 3 H, J=7.6 Hz, CH$_3$CH$_2$CH$_2$CH$_2$); 1.26-1.33 (m, 2 H, CH$_3$CH$_2$CH$_2$CH$_2$); 1.40-1.48 (m, 2 H, CH$_3$CH$_2$CH$_2$CH$_2$); 2.61 (d, 3 H, J=4.5 Hz, N(CH$_3$)$_2$); 2.78 (d, 3 H, J=4.5 Hz, N(CH$_3$)$_2$); 3.10-3.20 (m, 2 H, CH$_3$CH$_2$CH$_2$CH$_2$); 3.87(s, 3 H, NCH$_3$); 5.80 (d, 1 H, J=9.1 Hz, CHN(CH$_3$)$_2$); 6.79 (d, 1 H, J=3.8 Hz, N(CH$_3$)]—CCHCHC—[); 6.90 (d, 1 H, J=3.8 Hz, N(CH$_3$)]—CCHCHC—[); 7.36-7.42 (m, 1 H, Ph); 7.42-7.48 (m, 2 H, Ph); 7.69-7.78 (m, 2 H, Ph); 8.01-8.07 (m, 1 H, NH); 11.74(s, 1 H, HCl).

Example 11

[5-(Dimethylamino-phenyl-methyl)-1-methyl-1H-pyrrol-2-yl]-pyrrolidin-1-yl-methanone hydrochloride $^1$H-NMR reveals two rotamers in the ratio of approx. 4:1. Only the signals for the compound in excess are stated.

δ ([MSO, 600 MHz)=1.73-1.92 (m, 4 H, N(CH$_2$)$_2$(CH$_2$)$_2$); 2.61 (d, 3 H, J=4.5 Hz, N(CH$_3$)$_2$); 2.79 (d, 3 H, J=4.5 Hz, N(CH$_3$)$_2$); 3.34-3.61 (m, 4 H, N(CH$_2$)$_2$(CH$_2$)$_2$); 3.73 (s, 3 H, NCH$_3$); 5.81 (d, 1 H, J=9.1 Hz, CHN(CH$_3$)$_2$); 6.56 (d, 1 H, J=3.8 Hz, N(CH$_3$)]—CCHCHC—[); 6.93 (d, 1 H, J=3.8 Hz, N(CH$_3$)]—CCHCHC); 7.38-7.52 (m, 3 H, Ph); 7.72-7.81 (m, 2 H, Ph); 11.75 (s, 1 H, HCl).

Example 12

(5-Butylcarbamoyl-1-methyl-1H-pyrrol-2-yl)-dimethylamino-acetic acid ethyl ester hydrochloride δ (DMSO, 600 MHz)=0.90 (t, 3 H, J=7.5 Hz, CH$_3$CH$_2$CH$_2$CH$_2$); 1.22 (t, 3 H, J=6.8 Hz, CH$_3$CH$_2$CO$_2$); 1.28-1.34 (m, 2 H, CH$_3$CH$_2$CH$_2$CH$_2$); 1.44-1.49 (m, 2 H, CH$_3$CH$_2$CH$_2$CH$_2$); 2.62 (br. s, 3 H, N(CH$_3$)$_2$); 2.79 (br. s, 3 H, N(CH$_3$)$_2$); 3.12-3.22 (m, 2 H, CH$_3$CH$_2$CH$_2$CH$_2$); 3.85 (s, 3 H, NCH$_3$); 4.17-4.24 (m, 1 H, CH$_3$CH$_2$CO$_2$); 4.24-4.32 (m, 1 H, CH$_3$CH$_2$CO$_2$); 5.22-5.32 (m, 1 H, CHN(CH$_3$)$_2$); 6.79-6.84 (m, 1 H, N(CH$_3$)]—CCHCHC—[); 7.11-7.17 (m, 1 H, N(CH$_3$)]—CCHCHC); 8.10-8.18 (m, 1 H, NH); 10.59 (s, 1 H, HCl).

Example 13

(5-Cyclohexylcarbamoyl-1-methyl-1H-pyrrol-2-yl)-dimethylamino-acetic acid ethyl ester hydrochloride $^1$H-NMR reveals two rotamers in the ratio of approx. 4:1. Only the signals for the compound in excess are stated.

δ (DMSO, 600 MHz)=1.06-1.15 (m, 1 H, NH]—CH(CH$_2$)$_2$(CH$_2$)$_2$CH$_2$—[); 1.18 (t, 3 H, J=6.8 Hz, CH$_3$CH$_2$CO$_2$); 1.25-1.34 (m, 5 H, NH]—CH(CH$_2$)$_2$(CH$_2$)$_2$CH$_2$—[); 1.67-1.83 (m, 4 H, NH]—CH(CH$_2$)$_2$(CH$_2$)$_2$CH$_2$); 2.60 (br. s, 3 H, N(CH$_3$)$_2$); 2.94 (br. s, 3 H, N(CH$_3$)$_2$); 3.47-3.62 (m, 1 H, NH]—CH(CH$_2$)$_2$(CH$_2$)$_2$CH$_2$—[); 3.95 (s, 3 H, NCH$_3$); 4.16-4.32 (m, 1 H, CH$_3$CH$_2$CO$_2$); 5.60-5.71 (m, 1 H, CHN(CH$_3$)$_2$); 6.30-6.40 (m, 1 H, N(CH$_3$)]—CCHCHC—[); 6.79-6.85 (m, 1 H, N(CH$_3$)]—CCHCHC—[); 7.89-7.99 (m, 1 H, NH); 11.08(s, 1 H, HCl).

Example 14

(5-Butylcarbamoyl-1-methyl-1H-pyrrol-2-yl)-piperidin-1-yl-acetic acid ethyl ester hydrochloride δ (DMSO, 600 MHz)=0.90 (t, 3 H, J=7.2 Hz, CH$_3$CH$_2$CH$_2$CH$_2$); 1.22 (t, 3 H, J=7.2 Hz, CH$_3$CH$_2$CO$_2$); 1.26-1.38 (m, 2 H, CH$_3$CH$_2$CH$_2$CH$_2$); 1.42-1.51 (m, 2 H, CH$_3$CH$_2$CH$_2$CH$_2$); 1.63-1.71 (m, 2 H, N(CH$_2$)$_2$(CH$_2$)$_2$CH$_2$); 1.72-1.90 (m, 4 H, N(CH$_2$)$_2$(CH$_2$)$_2$CH$_2$); 2.89-3.02 (m, 2 H, N(CH$_2$)$_2$(CH$_2$)$_2$CH$_2$); 3.10-3.24 (m, 2 H, N(CH$_2$)$_2$(CH$_2$)$_2$CH$_2$); 3.37-3.41 (m, 1 H, CH$_3$CH$_2$CH$_2$CH$_2$); 3.42-3.49 (m, 1 H, CH$_3$CH$_2$CH$_2$CH$_2$); 3.84 (s, 3 H, NCH$_3$); 4.15-4.22 (m, 1 H, CH$_3$CH$_2$CO$_2$); 4.25-4.32 (m, 1 H, CH$_3$CH$_2$CO$_2$); 5.19-5.25 (m, 1 H, CHN(CH$_2$)$_2$(CH$_2$)$_2$CH$_2$); 6.77-6.83 (m, 1 H, N(CH$_3$)]—CCHCHC—[); 7.09-7.15 (m, 1 H, N(CH$_3$)]—CCHCHC); 8.11-8.18 (m, 1 H, NH); 10.38 (s, 1 H, HCl).

Example 15

(5-Cyclohexylcarbamoyl-1-methyl-1H-pyrrol-2-yl)-piperidin-1-yl-acetic acid ethyl ester hydrochloride δ (DMSO, 600 MHz)=1.05-1.16 (m, 1 H, NH]—CH(CH$_2$)$_2$(CH$_2$)$_2$CH$_2$—[); 1.22 (t, 3 H, J=6.8 Hz, CH$_3$CH$_2$CO$_2$); 1.24-1.36 (m, 5 H, NH]—CH(CH$_2$)$_2$(CH$_2$)$_2$CH$_2$—[); 1.56-1.86 (m, 10 H, NH]—CH(CH$_2$)$_2$(CH$_2$)$_2$CH$_2$, N(CH$_2$)$_2$(CH$_2$)$_2$CH$_2$, N(CH$_2$)$_2$(CH$_2$)$_2$CH$_2$); 2.63-2.72 (m, 1 H, N(CH$_2$)$_2$(CH$_2$)$_2$CH$_2$); 2.91-2.98 (m, 1 H, N(CH$_2$)$_2$(CH$_2$)$_2$CH$_2$); 3.41-3.48 (m, 1 H, N(CH$_2$)$_2$(CH$_2$)$_2$CH$_2$); 3.62-3.72 (m, 1H, N(CH$_2$)$_2$(CH$_2$)$_2$CH$_2$); 3.84 (s, 3 H, NCH$_3$); 4.15-4.20 (m, 1 H, CH$_3$CH$_2$CO$_2$); 4.27-4.33 (m, 1 H, CH$_3$CH$_2$CO$_2$); 5.21 (d, 1 H, J=5.3 Hz, CHN(CH$_2$)$_2$(CH$_2$)$_2$CH$_2$); 6.81-6.86 (m, 1 H, N(CH$_3$)]—CCHCHC—[); 7.08-7.14 (m, 1 H, N(CH$_3$)]—CCHCHC); 7.92 (d, 1 H, J=7.5 Hz, NH); 10.22 (s, 1 H, HCl).

Pharmacological Investigations:

a) Affinity for ORL-1 Receptor

The affinity of the 5-aminomethyl-1H-pyrrole-2-carboxylic acid amides according to the invention for the ORL-1 receptor was determined as described above. The value for a selected compound is shown in Table 4 below.

TABLE 4

| Compound according to Example | Human ORL-1 inhibition [%] |
|---|---|
| 9 | 23 | b) Affinity for μ Receptor

The affinity of the 5-aminomethyl-1H-pyrrole-2-carboxylic acid amides according to the invention for the μ receptor was determined as described above. The values for some selected compounds are shown in Table 5 below.

TABLE 5

| Compound according to Example | Human ORm NaI inhibition [%] | Human ORm NaI Ki [μM] |
|---|---|---|
| 1 | 62 | 0.16 |
| 2 | 49 | 0.36 |
| 4 | 80 | 0.79 |
| 5 | 62 | * |
| 7 | 65 | 1.0 |
| 9 | 76 | * |
| 11 | 33 | * |

* not determined c1) 5-HT Uptake Inhibition

5-HT uptake inhibition of the 5-aminomethyl-1H-pyrrole-2-carboxylic acid amides according to the invention was determined as described above. The values for some selected compounds are shown in Table 6 below.

TABLE 6

| Compound according to Example | 5-HT uptake inhibition [%] conc. 10 |
|---|---|
| 1 | 57 |
| 2 | 52 |
| 4 | 72 |
| 5 | 57 |
| 6 | 51 |
| 7 | 93 |
| 8 | 79 |
| 11 | 54 | c2) Noradrenalin Reuptake Inhibition

The noradrenalin reuptake inhibition of the 5-aminomethyl-1H-pyrrole-2-carboxylic acid amides according to the invention was determined as described above. The values for some selected compounds are shown in Table 7 below.

TABLE 7

| Compound according to Example | Noradrenalin uptake inhibition [%] conc. 10 |
|---|---|
| 1 | 80 |
| 2 | 72 |
| 3 | 38 |
| 4 | 93 |
| 5 | 86 |
| 6 | 83 |
| 7 | 95 |
| 8 | 43 |
| 9 | 70 |
| 10 | 52 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereto.

What is claimed is:

1. A 5-aminomethyl-1H-pyrrole-2-carboxylic acid amide compound corresponding to formula I,

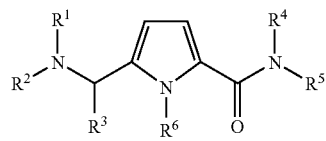

wherein, $R^1$ denotes hydrogen; a linear or branched, saturated or unsaturated, substituted or unsubstituted aliphatic group; a saturated or unsaturated, substituted or unsubstituted cycloaliphatic group which may include at least one heteroatom as a ring member and which may be attached via a substituted or unsubstituted alkylene group; a substituted or unsubstituted aryl or heteroaryl group or a substituted or unsubstituted aryl or heteroaryl group attached via a substituted or unsubstituted alkylene group, $R^2$ denotes hydrogen; a linear or branched, saturated or unsaturated, substituted or unsubstituted aliphatic group; a saturated or unsaturated, substituted or unsubstituted cycloaliphatic group which may include at least one heteroatom as a ring member and which may be attached via a substituted or unsubstituted alkylene group; a substituted or unsubstituted aryl or heteroaryl group or a substituted or unsubstituted aryl or heteroaryl group attached via a substituted or unsubstituted alkylene group, $R^1$ and $R^2$, together with the nitrogen atom joining them as a ring member, form a saturated or unsaturated, substituted or unsubstituted cycloaliphatic group which may include at least one further heteroatom as a ring member, $R^3$ denotes a substituted or unsubstituted aryl or heteroaryl group, an ester group or a carboxy group, $R^4$ and $R^5$ may be identical or different, and denote hydrogen; a linear or branched, saturated or unsaturated, substituted or unsubstituted aliphatic group; a saturated or unsaturated, substituted or unsubstituted cycloaliphatic group which may include at least one heteroatom as a ring member and which may be attached via a substituted or unsubstituted alkylene group; a substituted or unsubstituted aryl or heteroaryl group or a substituted or unsubstituted aryl or heteroaryl group attached via a substituted or unsubstituted alkylene group, or $R^4$ and $R^5$, together with the nitrogen atom joining them as a ring member, form a saturated or unsaturated, substituted or unsubstituted cycloaliphatic group which may include at least one further heteroatom as a ring member, and $R^6$ denotes a linear or branched, saturated or unsaturated, substituted or unsubstituted aliphatic group; a saturated or unsaturated, substituted or unsubstituted cycloaliphatic group which may include at least one heteroatom as a ring member and which may be attached via a substituted or unsubstituted alkylene group; a substituted or unsubstituted aryl or heteroaryl group or a substituted or unsubstituted aryl or heteroaryl group attached via a substituted or unsubstituted alkylene group, a free base, a physiologically acceptable salt, a pure enantiomer or pure diastereoisomer, a mixture of stereoisomers, a solvate, or a hydrate thereof.

2. The compound of claim 1, wherein said compound is present in the form of a free base.

3. The compound of claim 1, wherein said compound is present in the form of an acid addition salt.

4. The compound of claim 1, wherein said compound is present in the form of a pure enantiomer or pure diastereoisomer.

5. The compound of claim 1, wherein said compound is present in the form of a mixture of stereoisomers.

6. The compound of claim 1, wherein said compound is present in the form of a racemic mixture.

7. The compound of claim 1, wherein said compound is present in the form of a solvate.

8. The compound of claim 1, wherein said compound is present in the form of a hydrate.

9. The compound of claim 1, wherein $R^1$ denotes hydrogen, a linear or branched, saturated or unsaturated, substituted or unsubstituted aliphatic $C_{1-6}$ group; a saturated or unsaturated, substituted or unsubstituted cycloaliphatic $C_{3-8}$ group which may include at least one heteroatom as a ring member and may be attached via a substituted or unsubstituted $C_{1-3}$ alkylene group; a substituted or unsubstituted, five- or six-membered aryl or heteroaryl group or a substituted or unsubstituted, five- or six-membered aryl or heteroaryl group attached via a substituted or unsubstituted $C_{1-3}$ alkylene group.

10. The compound of claim 9, wherein the substituted or unsubstituted $C_{1-3}$ alkylene group which attaches the substituted or unsubstituted five- or six-membered aryl or heteroaryl group is a linear or branched, saturated aliphatic $C_{1-3}$ group.

11. The compound of claim 10, wherein the substituted or unsubstituted $C_{1-3}$ alkylene group which attaches the substituted or unsubstituted five- or six-membered aryl or heteroaryl group is a methyl group.

12. The compound of claim 1, wherein $R^2$ denotes a linear or branched, saturated or unsaturated, substituted or unsubstituted aliphatic $C_{1-6}$ group; a saturated or unsaturated, substituted or unsubstituted cycloaliphatic $C_{3-8}$ group which may include at least one heteroatom as a ring member and may be attached via a substituted or unsubstituted $C_{1-3}$ alkylene group; a substituted or unsubstituted five- or six-membered aryl or heteroaryl group or a substituted or unsubstituted five- or six-membered aryl or heteroaryl group attached via a substituted or unsubstituted $C_{1-3}$ alkylene group.

13. The compound of claim 12, wherein the substituted or unsubstituted $C_{1-3}$ alkylene group which attaches the substituted or unsubstituted five- or six-membered aryl or heteroaryl group is a linear or branched, saturated aliphatic $C_{1-3}$ group.

14. The compound of claim 13, wherein the substituted or unsubstituted $C_{1-3}$ alkylene group which attaches the substituted or unsubstituted five- or six-membered aryl or heteroaryl group is a methyl group.

15. The compound of claim 1, wherein $R^1$ and $R^2$, together with the nitrogen atom joining them as a ring member, form a saturated or unsaturated, substituted or unsubstituted, five- or six-membered cycloaliphatic group, which may include at least one further heteroatom selected from the group consisting of N, O and S as a ring member.

16. The compound of claim 1, wherein $R^1$ and $R^2$, together with the nitrogen atom joining them as a ring member, form a saturated, five- or six-membered cycloaliphatic group which comprises oxygen as a further ring member.

17. The compound of claim 1, wherein $R^1$ and $R^2$ together denote a $(CH_2)_4$, $(CH_2)_5$ or $(CH_2)_2$—O—$(CH_2)_2$ group which, with the nitrogen atom joining them as a ring member, forms a heterocycle.

18. The compound of claim 1, wherein $R^3$ denotes a substituted or unsubstituted, five- or six-membered aryl or heteroaryl group or an aryl ester, heteroaryl ester or alkyl ester group.

19. The compound of claim 18, wherein $R^3$ denotes a substituted or unsubstituted phenyl group or an alkyl ester group with $C_{1-3}$ in the alkyl moiety.

20. The compound of claim 18, wherein $R^3$ denotes an alkyl ester group with $C_{1-2}$ in the alkyl moiety.

21. The compound of claim 1, wherein $R^4$ and $R^5$, may be the same or different, and denote hydrogen; a linear or branched, saturated or unsaturated, substituted or unsubstituted aliphatic $C_{1-6}$ group; a saturated or unsaturated, substituted or unsubstituted cycloaliphatic $C_{3-8}$ group which may include at least one heteroatom as a ring member and which may be attached via an substituted or unsubstituted $C_{1-3}$ alkylene group; a substituted or unsubstituted, five- or six-membered aryl or heteroaryl group or a substituted or unsubstituted, five- or six-membered aryl or heteroaryl group attached via an substituted or unsubstituted $C_{1-3}$ alkylene group.

22. The compound of claim 1, wherein $R^4$ and $R^5$, together with the nitrogen atom joining them as a ring member, form a saturated or unsaturated, substituted or unsubstituted, five-, six- or seven-membered cycloaliphatic group, which may include at least one further heteroatom selected from the group consisting of N, O and S as a ring member.

23. The compound of claim 1, wherein $R^4$ and $R^5$, together with the nitrogen atom joining them as a ring member, form a saturated, five- or six-membered cycloaliphatic group which includes oxygen as a further ring member.

24. The compound of claim 1, wherein $R^4$ and $R^5$, together denote a $(CH_2)_4$, $(CH_2)_5$ or $(CH_2)_2$—O—$(CH_2)_2$ group which, together with the nitrogen atom joining them as a ring member, forms a heterocycle.

25. The compound of claim 1, wherein $R^6$ denotes a linear or branched, saturated or unsaturated, substituted or unsubstituted aliphatic $C_{1-6}$ group; a saturated or unsaturated, substituted or unsubstituted cycloaliphatic $C_{3-8}$ group which may include at least one heteroatom as a ring member and which may be attached via a substituted or unsubstituted $C_{1-3}$ alkylene group; an substituted or unsubstituted, five- or six-membered aryl or heteroaryl group, a substituted or unsubstituted, five- or six-membered aryl or heteroaryl group attached via a substituted or unsubstituted $C_{1-3}$ alkylene group.

26. The compound of claim 25, wherein the substituted or unsubstituted $C_{1-3}$ alkylene group which attaches the substituted or unsubstituted five- or six-membered aryl or heteroaryl group is a linear or branched, saturated aliphatic $C_{1-3}$ group.

27. The compound of claim 25, wherein the substituted or unsubstituted $C_{1-3}$ alkylene group which attaches the five- or six-membered aryl or heteroaryl group is a methyl group.

28. The compound of claim 1, wherein said compound is selected from the group consisting of:
- 5-[dimethylamino-(4-fluoro-phenyl)-methyl]-1H-methyl-1H-pyrrole-2-carboxylic acid cyclohexylamide,
- 5-[dimethylamino-(4-fluoro-phenyl)-methyl]-1-methyl-1H-pyrrole-2-carboxylic acid butylamide,
- {5-[dimethylamino-(4-fluoro-phenyl)-methyl]-1H-methyl-1H-pyrrol-2-yl}-pyrrolidin-1-yl-methanone,
- 5-[dimethylamino-(4-bromo-phenyl)-methyl]-1-methyl-1H-pyrrole-2-carboxylic acid cyclohexylamide,
- 5-[dimethylamino-(4-bromo-phenyl)-methyl]-1-methyl-1H-pyrrole-2-carboxylic acid butylamide,
- {5-[(4-bromo-phenyl)-dimethylamino-methyl]-1H-methyl-1H-pyrrol-2-yl}-pyrrolidin-1-yl-methanone,
- 5-[(4-bromo-phenyl)-dimethylamino-methyl]-1H-methyl-1H-pyrrole-2-carboxylic acid phenethyl-amide,
- {5-[(4-bromo-phenyl)-dimethylamino-methyl]-1-methyl-1H-pyrrol-2-yl}-morpholin-4-yl-methanone,
- 5-(dimethylamino-phenyl-methyl)-1-methyl-1H-pyrrole-2-carboxylic acid cyclohexylamide,
- 5-(dimethylamino-phenyl-methyl)-1-methyl-1H-pyrrole-2-carboxylic acid butylamide,
- [5-(dimethylamino-phenyl-methyl)-1-methyl-1H-pyrrol-2-yl]-pyrrolidin-1-yl-methanone,
- (5-butylcarbamoyl-1-methyl-1H-pyrrol-2-yl)-dimethylamino-acetic acid ethyl ester,
- (5-cyclohexylcarbamoyl-1-methyl-1H-pyrrol-2-yl)-dimethylamino-acetic acid ethyl ester,
- (5-butylcarbamoyl-1-methyl-1H-pyrrol-2-yl)-piperidin-1-yl-acetic acid ethyl ester and
- (5-cyclohexylcarbamoyl-1-methyl-1H-pyrrol-2-yl)-piperidin-1-yl-acetic acid ethyl ester.

29. A process for producing a 5-aminomethyl-1H-pyrrole-2-carboxylic acid amide compound according to claim 1, comprising reacting a substituted 1H-pyrrole-2-carboxylic acid amide corresponding to formula II

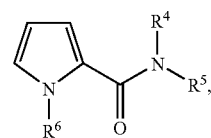

II with an iminium salt corresponding to formula III,

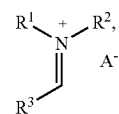

III wherein $A^-$ denotes a suitable anion.

30. The process of claim 29, wherein $A^-$ is selected from the group consisting of $Cl^-$, $AlCl_4^-$, $Br^-$, $I^-$ or $CF_3$—$SO_3^-$ (triflate anion).

31. The process of claim 29, further comprising the step of isolating the compound according to claim 1.

32. A pharmaceutical preparation comprising at least one substituted 5-aminomethyl-1H-pyrrole-2-carboxylic acid amide compound according to claim 1, and at least one physiologically acceptable auxiliary substance.

33. A method of treating pain in a mammal, said method comprising administering to said mammal an effective amount of a 5-aminomethyl-1H-pyrrole-2-carboxylic acid amide compound of claim 1.

* * * * *